United States Patent
Carlberg et al.

(10) Patent No.: US 9,498,762 B2
(45) Date of Patent: Nov. 22, 2016

(54) SYSTEM AND PROCESS FOR PRODUCING AN OXIRANE

(75) Inventors: Philip J. Carlberg, Lake Jackson, TX (US);
(Continued)

(73) Assignee: BLUE CUBE IP LLC, Midland, MI (US)

( * ) Notice: Subject to any disclaimer, the term of this patent is extended or adjusted under 35 U.S.C. 154(b) by 644 days.

(21) Appl. No.: 13/983,361

(22) PCT Filed: Feb. 3, 2012

(86) PCT No.: PCT/IT2012/000036
§ 371 (c)(1),
(2), (4) Date: Aug. 2, 2013

(87) PCT Pub. No.: WO2012/104886
PCT Pub. Date: Aug. 9, 2012

(65) Prior Publication Data
US 2013/0302216 A1    Nov. 14, 2013

Related U.S. Application Data

(60) Provisional application No. 61/439,718, filed on Feb. 4, 2011.

(51) Int. Cl.
*B01J 8/20* (2006.01)
*B01J 8/02* (2006.01)
(Continued)

(52) U.S. Cl.
CPC .............. *B01J 8/20* (2013.01); *B01D 11/0488* (2013.01); *B01D 11/0492* (2013.01);
(Continued)

(58) Field of Classification Search
CPC .................. C07D 301/12; C07D 301/32; B01J 8/02; B01J 8/0278; B01J 8/20; B01J 2219/00247; B01J 2219/00245
See application file for complete search history.

(56) References Cited

U.S. PATENT DOCUMENTS 3,928,393 A * 12/1975 Herzog ............... C07C 407/006
549/529
4,117,066 A    9/1978 Mollet et al.
(Continued)

FOREIGN PATENT DOCUMENTS

CN    101747296    6/2010
CN    101747297    6/2010
(Continued)

OTHER PUBLICATIONS

Thiele, G.F. and Roland, E., "Propylene epoxidation with hydrogen peroxide and titanium silicalite catalyst: Activity, deactivation, and regeneration of the catalyst," Journal of Moelcular Catalysis A: Chemical 117 (1997) 351-356.
(Continued)

*Primary Examiner* — Lessanework Seifu
(74) *Attorney, Agent, or Firm* — Polsinelli PC

(57) ABSTRACT

Embodiments of the present disclosure are directed to a system and a process for producing an oxirane. For the various embodiments, the system and process of the present disclosure includes: a reaction vessel having a reaction mixture of an olefin, a peroxide compound, a solvent mixture with an alcohol and a non-reactive co-solvent, a solid phase, and reaction products of the reaction mixture, where the reaction products include an oxirane; a separation vessel coupled to the reaction vessel, where an effluent of the reaction mixture and reaction products from the reaction vessel separates in the separation vessel into a liquid aqueous phase and a liquid organic phase; and an extraction vessel coupled to an outlet of the separation vessel, where the liquid aqueous phase taken from the outlet of the separation vessel mixes with an extraction solvent to extract oxirane from the aqueous phase.

12 Claims, 6 Drawing Sheets

(75) Inventors: Hannah L. Crampton, Lake Jackson, TX (US); Anna Forlin, Padua (IT); Esteban Pedernera, Stade (DE); Cesar E. Meza, Pearland, TX (US)

(51) Int. Cl.
*C07D 301/12* (2006.01)
*C07D 301/32* (2006.01)
*B01D 11/04* (2006.01)
*B01J 19/00* (2006.01)

(52) U.S. Cl.
CPC ............. *B01J 8/0278* (2013.01); *B01J 19/00* (2013.01); *C07D 301/12* (2013.01); *C07D 301/32* (2013.01); *B01J 2219/00247* (2013.01)

(56) References Cited

U.S. PATENT DOCUMENTS

| | | | |
|---|---|---|---|
| 4,370,240 | A | 1/1983 | Brownell et al. |
| 5,252,758 | A | 10/1993 | Clerici et al. |
| 5,620,935 | A | 4/1997 | Thiele |
| 5,952,530 | A | 9/1999 | Argyropoulos |
| 6,063,941 | A | 5/2000 | Gilbeau |
| 6,169,050 | B1 | 1/2001 | Catinat et al. |
| 6,288,248 | B1 | 9/2001 | Strebelle et al. |
| 6,818,132 | B2 | 11/2004 | Haubs et al. |
| 7,323,578 | B2 | 1/2008 | Catinat et al. |
| 7,705,167 | B2 | 4/2010 | Shinohara et al. |
| 7,838,455 | B2 | 11/2010 | Kwak et al. |
| 8,534,963 | B2 | 9/2013 | Luik |
| 2006/0016760 | A1 | 1/2006 | Bozak et al. |
| 2008/0095677 | A1* | 4/2008 | McSherry ............. C07C 407/00 422/424 |
| 2010/0264091 | A1 | 10/2010 | Nazzer |
| 2011/0137054 | A1 | 6/2011 | Postma et al. |
| 2012/0130095 | A1 | 5/2012 | Crampton et al. |

FOREIGN PATENT DOCUMENTS

| | | |
|---|---|---|
| CN | 101279958 | 10/2010 |
| DE | 19962719 | 6/2001 |
| WO | 2008087657 | 7/2008 |
| WO | 2009063487 | 5/2009 |

OTHER PUBLICATIONS

Clerici, Mario G.; Ingallina, Patrizia. "Epoxidation of lower olefins with hydrogen peroxide and titanium silicalite." Journal of Catalysis, 1993, 140, 71-83.

Zhang, Zhaoguang; Kang, Jingna, Yaquan. "Effects of organic solvent addition on the epoxidation of propene catalyzed by TS-1." Reaction of Kinetics and Catalysis Letters 2007, 92(1), 49-52.

Gea Westfalia Separator; "Separation, Solution, Success"; 2010.

* cited by examiner

SYSTEM AND PROCESS FOR PRODUCING AN OXIRANE

This application is a National Stage application under 35 U.S.C. 371 of PCT/IT2012/000036, filed on Feb. 3, 2012 and published as WO 2012/104886 on Aug. 9, 2012, which claims the benefit of U.S. Provisional Application Ser. No. 61/439,718 filed Feb. 4, 2011, the entire contents of which are incorporated herein by reference in its entirety.

CROSS-REFERENCE TO RELATED APPLICATIONS

This application claims the benefit under 35 U.S.C. §119(e) of U.S. Provisional Patent Application No. 61/439,718, filed Feb. 4, 2011, which is incorporated herein by reference in its entirety.

FIELD OF DISCLOSURE

Embodiments of the present disclosure are directed to a system and a process for producing an oxirane.

BACKGROUND

Oxiranes are valuable chemicals and are useful in a variety of end use applications. Epichlorohydrin, for example, is an oxirane and a valuable chemical commodity used extensively to make epoxy resins on a commercial scale. Currently, a "chlorohydrin" process is employed for manufacturing epichlorohydrin. The process begins with the chlorohydrination of allyl chloride by reaction with an aqueous dispersion of chlorine in water. This process forms an isomeric mixture of 1,2- and 1,3-dichlorohydrin, which is subjected to dehydrochlorination in caustic solution to yield epichlorohydrin. The chlorohydrin process is used to make over 95% of epichlorohydrin produced globally, but this known process suffers from the disadvantages of producing high levels of chlorinated organic compounds and salt in waste streams, and of producing large amounts of waste water.

There are several known processes in the art that use peroxide, such as hydrogen peroxide ($H_2O_2$), to produce an oxirane, including for example epichlorohydrin. Such processes are described in: Clerici et al., "Epoxidation of Lower Olefins with Hydrogen Peroxide and Titanium Silicalite," Journal of Catalysis, 1993, 140, 71-83; U.S. Pat. No. 7,323,578; EP Patent Application Publication No. 1993/0549013 A1; Pandey et al., "Eco-friendly Synthesis of Epichlorohydrin Catalyzed by Titanium Silicalite (TS-1) Molecular Sieve and Hydrogen Peroxide," Catalysis Communications, 2007, 8, 379-382; Chinese Patent Application No. CN 200710039080.1; Zhang et al., "Effects of Organic Solvent Addition on the Epoxidation of Propene Catalyzed by TS-1," Reaction Kinetics and Catalysis Letters, 2007, 92(1), 49-54; Li, et al., "Epoxidation of Allyl Chloride to Epichlorohydrin by a Reversible Supported Catalyst with $H_2O_2$ Under Solvent-Free Conditions," Organic Process Research & Development, 2006, 10, 876-880; Patent application PCTUS/08/080, titled "Process for epoxidizing olefins with hydrogen peroxide using supported oxo-diperoxo tungstate catalyst complex"; and U.S. Pat. No. 6,288,248 B1.

For epoxidizing some olefins, such as allyl chloride, using a peroxide reaction catalyzed by a titanium silicalite, it is well known that methanol is a necessary component of the peroxide reaction to obtain high activity. Generally, methanol must be used in large excesses in the known processes. This results in the formation of byproducts from the reaction of methanol and water, which is solubilized in the organic phase by methanol, with an oxirane. It is estimated that the use of these large quantities of methanol would result in the construction of large towers and the consumption of a large amount of energy for the purification of the oxirane product if produced on a commercial scale. Additionally, a titanium silicalite-1 (TS-1) catalyst used under these conditions would deactivate in a matter of hours; and subsequently, would have to be fully regenerated by calcination. Furthermore, the high concentration of methanol promotes the formation of by-products through the reaction of the oxirane product with methanol.

Some of the problems of the known processes described above may be summarized as follows:

(1) The prior art processes use high levels of methanol. The high levels of methanol must be separated from the oxirane product and recycled which creates a high energy use for the process and associated high costs. The high concentrations of methanol also lead to high levels of by-products through solvolysis of the oxirane by methanol.

(2) An organic solvent is typically added in the prior art processes following the reaction instead of (luring the reaction. This allows oxirane product to contact and react with components in the reaction mixture such as water and an alcohol phase to form non-usable byproducts. The byproducts decrease the yield of the desired oxirane product, and must be purged from the process.

It is desired to provide a system and a process for preparing an oxirane product that can be operated at reaction conditions that do not have the problems of the above described processes; that still maintains a high catalyst activity; that increases the selectivity of the reaction; and that extends the lifetime of the catalyst without the need for any additional components which would have to be removed in a subsequent downstream process.

It is also desired to provide an epoxidation process for a system and a process of producing an oxirane product, such as epichlorohydrin, that utilizes a multiphase process instead of a single phase process; and that the system and the process produces less wastewater than other known processes.

SUMMARY

One or more embodiments of the present disclosure include a process and a system for producing an oxirane. For the various embodiments, the system includes: a reaction vessel having a reaction mixture of an olefin, a peroxide compound, a solvent mixture with an alcohol and a non-reactive co-solvent, a solid phase, and reaction products of the reaction mixture, where the reaction products include an oxirane; a separation vessel coupled to the reaction vessel, where an effluent of the reaction mixture and reaction products from the reaction vessel separates in the separation vessel into a liquid aqueous phase and a liquid organic phase; and an extraction vessel coupled to an outlet of the separation vessel, where the liquid aqueous phase taken from the outlet of the separation vessel mixes with an extraction solvent to extract oxirane from the aqueous phase.

In one or more embodiments, the solid phase has an affinity for the liquid aqueous phase, where both the liquid aqueous phase and the solid phase form a slurry that is taken from the outlet of the separation vessel and mixes with the extraction solvent to extract oxirane from the aqueous phase. In an additional embodiment, the reaction vessel can include a fixed bed, where the fixed bed includes and retains the solid phase in the reaction vessel.

In one or more embodiments, the extraction solvent used in the present disclosure can be the non-reactive co-solvent. In one or more embodiments, the extraction solvent can be used to extract an olefin from the liquid aqueous phase. In one or more embodiments, the extraction solvent can be different than the olefin. In one or more embodiments, the extraction solvent and the non-reactive co-solvent are both 1,2-dichlorobenzene.

In one or more embodiments, the system and process of the present disclosure can further include an exchange vessel holding a solid support with active sites that can bind iron ions. In one or more embodiments, the exchange vessel has an inlet that carries an organic stream including the olefin and iron ions, where the active sites on the solid support remove iron ions from the organic stream to provide an iron ion concentration of less than one weight percent based on the total weight of the organic stream, and where the exchange vessel has an outlet that connects to the reaction vessel that receives the organic stream having the olefin and the iron ion concentration of less than one weight percent. In one or more embodiments, the solid support in the exchange vessel can be in a fixed bed. In one or more embodiments, the solid support in the exchange vessel can be in a slurry.

In one or more embodiments, the system and process of the present disclosure can further include regenerating a first part of the solid phase suspended in the liquid aqueous phase from the separation vessel with a regeneration solution. For example, the first part of the solid phase can be contacted with a regeneration solution having an oxidizing agent concentration of less than 0.50 weight percent based on a total weight of the liquid regeneration solution, exclusive of the solid phase, to regenerate the solid phase. In an additional embodiment, the first part of the solid phase suspended in the liquid aqueous phase from the separation vessel can be regenerated by contacting the first part of the solid phase with a regeneration solution having a pH of less than 2. The regeneration of the solid phase may also include a washing step, e.g., a pre-regeneration and/or post-regeneration washing step, wherein in addition to contact with the regeneration solution, the solid phase is contacted with a washing solution that includes an organic compound. Examples of the organic compound include, but are not limited to, aliphatic, cyclic, aromatic, halogenated, supercritical, or alcoholic organic diluents. Water could be used alternatively. For one embodiment, the organic compound is methanol. For one or more embodiments, the catalyst undergoing regeneration is washed for a time period within a range of from 5 minutes to 60 minutes, preferably 30 minutes.

Alternative embodiments of the regeneration of the solid phase eliminate the washing step., i.e., the solid phase is not contacted with a washing solution either pre-regeneration and/or post-regeneration during regeneration. Instead, the solid phase is contacted with a regeneration solution that includes at least one oxidizing agent and an organic compound to regenerate the solid phase. In one example of this embodiment, the first part of the solid phase is contacted with a regeneration solution having an oxidizing agent concentration of 0.1 to 50 weight percent based on a total weight of the regeneration solution, exclusive of the solid phase, wherein the regenerating does not include washing in addition to contacting with the regeneration solution to regenerate the solid phase.

In one specific example, the oxirane is epichlorohydrin, the olefin is allyl chloride, and the peroxide compound is a hydrogen peroxide solution.

In one or more embodiments, the process of the present disclosure includes: providing the reaction mixture of the olefin, the peroxide compound, the solvent mixture with the alcohol and the non-reactive co-solvent, the solid phase, and reaction products of the reaction mixture that include the oxirane; separating an effluent containing the reaction products and the reaction mixture into a liquid aqueous phase and a liquid organic phase, where the solid phase has an affinity for the liquid aqueous phase; recovering the liquid aqueous phase including the oxirane and a first part of the solid phase; and extracting oxirane from the liquid aqueous phase with an extraction solvent. In the specific embodiment where the catalyst remains within the reactor, as for example with a fixed bed reactor, then the process of the present disclosure includes separating an effluent containing the reaction products and the reaction mixture into a liquid aqueous phase and a liquid organic phase; recovering the liquid aqueous phase including the oxirane; and extracting oxirane from the liquid aqueous phase with an extraction solvent.

In one or more embodiments, the process of the present disclosure can also include extracting the olefin from the liquid aqueous phase with the extraction solvent. In one or more embodiments, the process of the present disclosure can include separating the oxirane from the liquid organic phase. In one or more embodiments, the process of the present disclosure can include recycling at least a portion of liquid organic phase back to the reaction mixture in the reaction vessel.

In one or more embodiments, the process of the present disclosure can also include removing iron ions from an organic stream that includes the olefin and iron ions to provide an iron ion concentration of less than one weight percent based on the total weight of the organic stream; and providing the organic stream having the iron ion concentration of less than one weight percent to the reaction mixture. In one or more embodiments, removing the iron ions can include removing the iron ions with an ion exchange resin.

In one or more embodiments, the solid phase used with the reaction mixture can be a titanium silicalite catalyst. As discussed herein, the titanium silicalite catalyst can foul in the course of forming the reaction products (fouled during a reaction between the olefin and the peroxide compound to produce the oxirane). Embodiments of the present disclosure include a process for regenerating the titanium silicalite catalyst fouled in forming the reaction products. For example, the titanium silicalite catalyst can be regenerated according to the present disclosure by adding an oxidizing agent to a regeneration solution, and contacting the fouled titanium silicalite catalyst with the regeneration solution to provide a regenerated titanium silicalite catalyst. In addition, certain embodiments of the regeneration process of the present disclosure include subjecting the catalyst undergoing regeneration to a washing step, e.g., in such an embodiment, the regeneration solution includes an oxidizing agent concentration of less than 0.50 weight percent based a total weight of the regeneration solution. One or more embodiments can include including adjusting a pH of the regeneration solution to less than 2 prior to contacting the fouled titanium silicalite catalyst with the regeneration solution. Alternative embodiments of the regeneration process eliminate the washing step, i.e., the catalyst is not contacted with a washing solution pre-regeneration and/or post-regeneration. In such embodiments, the regeneration solution can include an oxidizing agent concentration of 0.5 to 5 weight percent (wt %) based on a total weight of the regeneration solution, exclusive of the titanium silicalite catalyst; and an organic compound at 5 to 95 weight percent (wt %) based on a total weight of the regeneration solution, exclusive of the titanium silicalite catalyst.

In one example, the regeneration solution includes an organic compound that is also present in the reactor section. The organic compound may optionally be increased in this stream prior to catalyst regeneration. The organic compound used in the regeneration can be recovered by distillation and recycled to the reaction section.

In one or more embodiments, the catalyst is a solid catalyst and is separated from the regeneration solution and recycled to the reactor.

The regeneration solution can be further processed, for example, for recovery of the organic compound.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The following drawings illustrate non-limiting embodiments of the present disclosure, wherein.

DEFINITIONS

Figure 1:
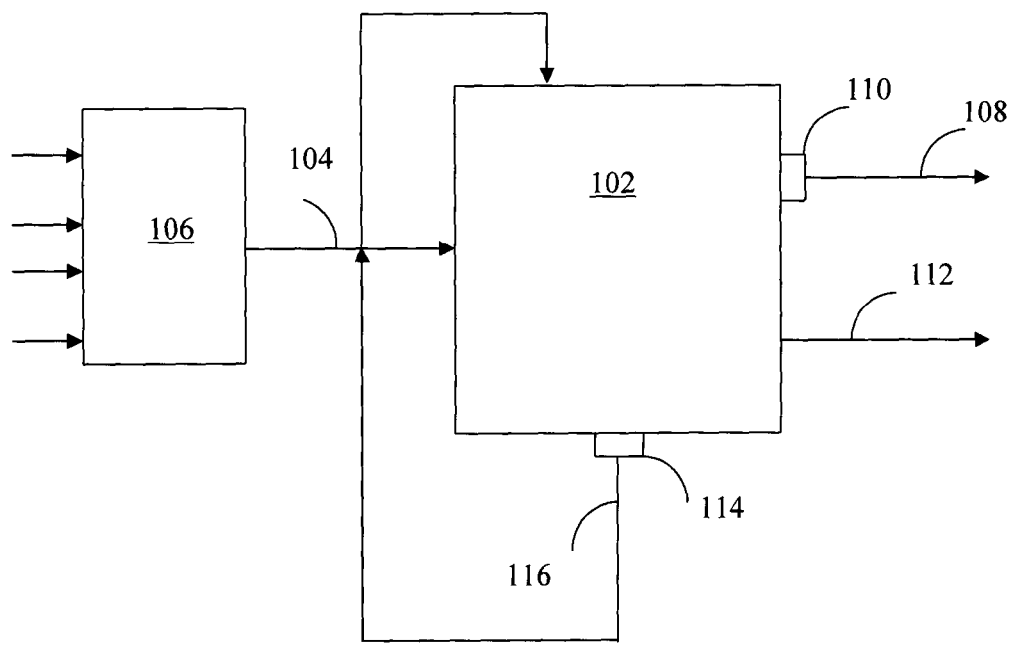
FIG. 1 illustrates a reaction vessel and a separation vessel for use with a system and process according to an embodiment of the present disclosure.

"Oxirane" refers to a compound in which an oxygen atom is directly attached to two adjacent or non-adjacent carbon atoms of a carbon chain or ring system. Epichlorohydrin, which is formed from an epoxidation reaction of allyl chloride, is an example of an oxirane.

"Supported solid" refers to an insoluble matrix (or support structure) formed from an organic polymer or inorganic material such as silicas or other minerals, for example, where the insoluble matrix includes active sites, such as functional groups, for the exchange of ions.

"Slurry" refers to a suspension of a solid (e.g., solid phase) in a liquid (e.g., liquid aqueous phase).

"Stabilizer" refers to a substance that tends to keep a compound, mixture, or solution from changing its form or chemical nature. Examples of such compounds include peroxides. For example, the stabilizer can be added to a peroxide solution, such as hydrogen peroxide, to reduce the rate of decomposition of the peroxide compound.

"Organic stream" refers to a mixture of at least an olefin, such as allyl chloride, and iron ions.

As used herein, "° C." is an abbreviation for degrees Celsius.

The term "and/or" means one, one or more, or all of the listed elements.

Unless otherwise indicated, all numbers expressing quantities of components, weight parts, temperatures, percentages, and so forth used in the specification and claims can be understood as being modified by the term "about."

As used herein, "a" "an" "the" "at least one" and "one or more" are used interchangeably. The terms "includes" and "comprises" and variations thereof do not have a limiting meaning where these terms appear in the description and claims. Thus, for example, a solvent mixture with an alcohol and a non-reactive co-solvent, a solid phase and reaction products of the reaction mixture can be interpreted to mean that the solvent mixture includes one or more alcohol(s), one or more non-reactive co-solvent(s), one or more solid phase(s) and one or more reaction products of the reaction mixture.

Also herein, the recitations of numerical ranges by endpoints include all numbers subsumed with that range (e.g. 1 to 5 includes 1, 1.5, 2, 2.75, 3, 3.8, 4, 5, etc.).

"Peroxide solution" refers to any solution including molecules containing one or more peroxide (—O—O—) functionalities, including organic or inorganic peroxides, peroxide adducts, or peracids.

"Iron ions" refers to the ions of iron including, but not limited to, $Fe^{3+}$, $Fe^{2+}$, $Fe^{1+}$ and combinations of $Fe^{3+}$, $Fe^{2+}$, $Fe^{1+}$ with other counterions such as e.g., $[FeCl_2]^+$.

"Piping" refers to a system of pipes used to convey fluids (e.g., a liquid) from one location to another location. Such piping can also include in-line components, such as fittings and valves that are used to couple the system of pipes.

DETAILED DESCRIPTION

In the following detailed description of the present disclosure, reference is made to an accompanying drawing that forms a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, chemical and/or structural changes may be made without departing from the scope of the present disclosure.

The figures herein follow a numbering convention in which the first digit or digits corresponds to the drawing figure number and the remaining digits identify an element in the drawing. Similar elements between different figures may be identified by the use of similar digits. For example, 106 may reference element "06" in FIG. 1, and a similar element may be referenced as 206 in FIG. 2. The proportion and the relative scale of the elements provided in the figures are intended to illustrate various embodiments of the present invention and are not to be used in a limiting sense.

Embodiments of the present disclosure provide a system and a process for producing an oxirane via a peroxide reaction. The problems of the prior art processes may be solved by the process of the present disclosure which provides an epoxidation process for producing an oxirane product, such epichlorohydrin, for example from allyl chloride and hydrogen peroxide, catalyzed by, for example, titanium silicalite-1 (TS-1), in a mixed solvent system. Unlike prior art systems and processes, however, the system and process of the present disclosure can produce the oxirane using lower amounts of total organic solvent (for example from 230-500 g solvent per kg of oxirane), and much lower amounts of methanol (for example, less than 100 g of methanol per kg of oxirane) than prior art processes.

The present disclosure provides such an advantage because it provides a system and a process that produces an oxirane that preferentially partitions (e.g., sequesters) into a liquid organic phase, thereby reducing its contact with water and thus reducing byproducts resulting from hydrolysis of the oxirane. This both increases the selectivity of the reaction and extends the lifetime of the catalyst without the need for any additional components in the reaction mixture, which would have to be removed in the downstream process. The multiphasic nature of the reaction mixture also facilitates the subsequent recovery of the oxirane, such as epichlorohydrin, by allowing a separation of a liquid aqueous phase and the liquid organic phase by, for example, decantation, prior to recovery of recyclable and useful product components from each stream.

In addition, the present disclosure is advantaged because the methanol concentrations presented in the present disclosure are lower than those presented in previously known processes. This helps to decrease losses of oxirane to solvolysis by methanol, thereby increasing the selectivity and maximizing peroxide use.

It has been found that while the present reaction is possible without the presence of methanol or solvent, the catalyst lifetime may be extremely short. The present disclosure is advantaged because, while the present disclosure process specifies a multiphase solvent system, the presence of a small amount of methanol, along with a non-reacting co-solvent, causes the oxirane produced to be preferentially sequestered into the organic phase, reducing the contact of the oxirane with water, and thus, reducing byproducts resulting from hydrolysis of the oxirane. This both increases the selectivity of the reaction and extends the lifetime of the catalyst.

Embodiments of the present disclosure provide for a system and a process for preparing an oxirane product from an olefin and a peroxide compound. The system includes, among other things, a reaction vessel, a separation vessel coupled to the reaction vessel and an extraction vessel coupled to the separation vessel, as will be more fully discussed herein. The reaction vessel contains a reaction mixture of an olefin, a peroxide compound, a solvent mixture with an alcohol and a non-reactive co-solvent, a solid phase, and reaction products of the reaction mixture. For the various embodiments, the reaction products in the reaction vessel include an oxirane.

As discussed more fully herein, the reaction mixture can include (a) at least one olefin wherein the olefin is selected from one of (i) an aliphatic olefin or substituted aliphatic olefin, (ii) a cycloaliphatic olefin, (iii) an aromatic olefin, (iv) a cycloaromatic olefin, and (v) mixtures thereof; with (b) at least one peroxide compound, in the presence of (c) the solid phase (e.g., at least one catalyst) and (d) in the presence of a solvent mixture; wherein the solvent mixture comprises at least (i) at least one alcohol or a combination of alcohols at a predetermined concentration and (ii) at least one non-reactive co-solvent at a predetermined concentration.

The olefin useful in the process of the present disclosure may comprise acyclic or cyclic aliphatic or aromatic olefins, including those which may contain multiple double bonds.

Examples of the olefin include, but are not limited to, chloride-butadiene and other linear dialkenes, cyclohexene and other cyclic alkenes and dialkenes, substituted alkenes, such as halogenated alkenes, styrene, divinylbenzene, dicyclopentadiene, other aromatic alkenes and mixtures thereof. Moreover, butenes, pentenes, hexenes, octenes, heptenes, 1-tridecene, mesityl oxide, isoprene, cyclo-octane, cyclohexene or bicyclic compounds such as norbornenes or pinenes may also be used. Other olefins useful in the process of the present disclosure may also include, for example, but are not limited to, other linear alkenes of formula $C_nH_{2n}$; butadiene and other linear dialkenes of formula $C_nH_{2n-2}$; cyclohexene and other cyclic alkenes and dialkenes; substituted alkenes, such as halogenated alkenes; styrene; divinylbenzene; dicyclopentadiene; and other aromatic alkenes and mixtures thereof. The system of the present disclosure may also be extended to the oxidation of aliphatic and aromatic alkanes and alcohols, such as, but not limited to, hexane, benzene, hexanol and phenol.

In a preferred embodiment of the present disclosure, the system may be used to epoxidize allyl chloride to epichlorohydrin using aqueous hydrogen peroxide and a titanium silicalite catalyst, TS-1.

The concentration of the at least one olefin is generally between about 10 percent by weight (wt %) to about 90 wt %, preferably between about 20 wt % to about 80 wt %, more preferably between about 30 wt % to about 70 wt %, and most preferably between about 40 wt % to about 65 wt %, based on the total weight of the composition which includes all of the components fed to the reaction vessel to form the reaction mixture including for example the weight all of the liquid components and the solid phase (e.g., catalyst) together herein "the total composition."

In one embodiment of the composition and process of the present disclosure, allyl chloride may be used as the olefin component; and the allyl chloride may be used in a concentration of about 40 wt % to about 65 wt % based on the weight of the total composition.

As used herein, "peroxide compound" refers to a compound containing one or more peroxide (—O—O—) functionalities, including organic or inorganic peroxides, peroxide adducts, peracids or combinations thereof. These can include, for example, but are not limited to, hydrogen peroxide, urea-hydrogen peroxide adduct, peracetic acid, and mixtures thereof.

The concentration of the peroxide compound may generally be between about 1% wt % to about 35 wt %, preferably between about 1 wt % to about 20 wt %, more preferably between about 1 wt % to about 10 wt %, and most preferably between about 1 wt % to about 7 wt %, based on the weight of the total composition.

A variety of peroxide compounds can be used in forming the reaction mixture of the present disclosure. Examples of the peroxide compounds useful in the present disclosure may include, but are not limited to, organic and/or inorganic hydroperoxides, such as hydrogen peroxide, tert-butyl hydroperoxide, ethylbenzene hydroperoxide, acetyl peroxide, benzoyl peroxide, methyl ethyl ketone peroxide, cumene peroxide and combinations thereof. In the present disclosure, preference is given to using hydrogen peroxide as the peroxide compound. The present disclosure as described herein, therefore, also provides a process for using hydrogen peroxide as the peroxide compound. Here, preference is given to using an aqueous hydrogen peroxide.

In one preferred embodiment of the present disclosure, an aqueous solution of hydrogen peroxide at about 30 wt % may be used such that the total amount of molecular hydrogen peroxide may be from about 1 wt % to about 7 wt %, based on the weight of the total composition.

The reaction procedure of the present disclosure in which the reaction of the oxirane with the hydroperoxide occurs under the pressure and temperature conditions indicated herein, is preferably carried out in the presence of a solid phase. For the various embodiments, the solid phase can be a catalyst used in the epoxidation reaction between the olefin and the peroxide compound. As used herein, a "catalyst" can be a homogeneous or heterogeneous catalyst appropriate for the epoxidation of an olefin. These may include, but are not limited to, soluble metal catalysts such as ligand-bound rhenium, tungsten, and manganese, and heterogenized forms of these, as well as solid silicalite catalysts that preferably contain titanium. These solid catalysts may have the crystal structure of ZSM-5, MCM-22, MCM-41, beta-zeolites, or amorphous titanium on silica.

Preference is given to a heterogeneous catalyst and particularly to a heterogeneous catalyst which comprises a porous oxide material such as zeolite. In general, the catalyst may include, but are not limited to, a titanium-, vanadium-, chromium-, niobium- or zirconium-containing zeolite as the porous oxide material.

Specific examples of suitable zeolites are titanium-, vanadium-, chromium-, niobium- and zirconium-containing zeolites having a pentasil zeolite structure, in particular the types assigned X-ray-crystallographically to the BEA, MOR, TON, MTW, FER, MFI, MEL, CHA, ERI, RHO, GIS, BOG, NON, EMT, HEU, KFI, FAU, DDR, MTT, RUT, RTH, LTL, MAZ, GME, NES, OFF, SGT, EUO, MFS, MWW or mixed MFI/MEL structures and also ITQ-4. It is also possible to use titanium-containing zeolites having the UTD-1, CIT-1 or CIT-5 structure in the process of the present disclosure. Further titanium-containing zeolites which might be mentioned are those having the ZSM-48 or ZSM-12 structure. Particular preference is given to using Ti zeolites having an MFI, MEL or mixed MFI/MEL structure in the process of the present disclosure. Further preference is given, specifically, to the Ti-containing zeolite catalysts which are generally designated as "TS-1", "TS-2" and "TS-3", and also Ti zeolites having a skeletal structure isomorphous with MWW-zeolite.

Particular preference is given to using a heterogeneous catalyst comprising the titanium-containing silicalite TS-1 in the process of the present disclosure.

It is possible to use the porous oxidic material itself as catalyst in the process of the present disclosure. However, it is of course also possible to use a shaped body comprising the porous oxidic material as catalyst. The shaped body from the porous oxidic material may be produced using known methods.

In embodiments employing a slurry continuous stirred tank reaction (CSTR) vessel, the concentration of the catalyst is generally between about 0.1 wt % to about 30 wt %, preferably between about 0.1 wt % to about 20 wt %, more preferably between about 0.1 wt % to about 10 wt %, and most preferably between about 0.5 wt % to about 5 wt %, based on the weight of the total composition.

As discussed herein, the solid phase can have an affinity for the liquid aqueous phase. As used herein, "affinity", or "chemical affinity", refers to an attraction or force by which dissimilar chemical species, e.g., the solid phase and liquid aqueous phase, have a tendency to associate with one another. In one or more embodiments the affinity for the solid phase for the liquid aqueous phase is due to van der Waals forces, hydrogen bonding, ionic interactions, and combinations thereof.

For one or more embodiments, the solid phase can include a polar group, a charged group, or a combination thereof to provide the affinity of the solid phase for the liquid aqueous phase. The polar group can include, but is not limited to —OH, —NR$_2$, phosphorous, sulfur, boron, and combinations thereof. The charged group can include, but is not limited to O$^-$, N$^-$, metal ions, and combinations thereof.

In a preferred embodiment of the present disclosure, the epoxidation of allyl chloride is converted to epichlorohydrin using hydrogen peroxide and a catalyst (e.g., the solid phase) such as titanium silicalite with MFI structure (TS-1) in one or more slurry continuous stirred tank reactor (CSTR) vessels. In this embodiment the concentration of the catalyst may preferably be between about 0.5 wt % to about 5 wt %, based on the weight of the total composition.

The catalyst is typically in solid form in the reaction mixture, while the reaction is carried out in the presence of two liquids, in general a liquid organic phase and a liquid aqueous phase. "Bisphasic" herein means at least two liquid phases. The solid form of the catalyst can be powders for slurry type reaction vessels or extrudates for fixed bed reaction vessels. In one embodiment of the present disclosure for a slurry reactor system, the solid phase (e.g, the catalyst) may be mixed with an organic phase, and then the aqueous phase may be added to the reaction mixture to prevent the decomposition of the peroxide compound. For the slurry reactor system, for example, the size of catalyst may be less than about 100 microns. The amounts of the individual components for the embodiment should be selected based on their physical properties such that when mixed together the liquid composition comprises at least two phases, organic and aqueous.

Component (d) of the present disclosure is a solvent mixture; wherein the solvent mixture comprises at least (i) at least one alcohol or a combination of two or more alcohols at a predetermined concentration, and (ii) at least one non-reactive co-solvent other than the solvent component (i) at a predetermined concentration; wherein the co-solvent has a different boiling point than the olefin and the oxirane. The solvent mixture is selected to include at least one solvent having properties such that the oxirane partitions into the at least one solvent present in the solvent mixture during the reaction. The at least one solvent is said to have a high affinity for the oxirane.

"Partitions" herein refers to the tendency of the oxirane product to be more soluble in the solvent mixture phase than in the other phase or phases present in the reaction mixture. It is quantified by the ratio of the oxirane product concentration in the solvent mixture phase to the total amount of oxirane product in the reaction mixture. Generally, the solvent is selected so that 90% or more of the oxirane product in the reaction mixture resides in the solvent mixture phase. Preferably, more than 99% of the oxirane product resides in the solvent mixture phase. Most preferably, 99.9% or more of the oxirane product resides in the solvent mixture phase.

For the embodiments of the present disclosure, an alcohol or a mixture of two or more alcohols can be used as the first solvent component of the solvent mixture. The alcohols may include, for example, lower alcohols such as alcohols having less than 6 carbon atoms, for example methanol, ethanol, propanols (e.g. isopropanol), butanols (e.g. tert-butanol) and pentanols and a combination of two or more of these alcohols; halogenated alcohols; and mixtures thereof. Preference is given to using a C1-C4 alcohol (or mixtures thereof), and more specifically to using methanol as the alcohol for the first solvent component. In particular, methanol not only acts as a solvent, but also acts as an activator for the catalyst.

The concentration of the alcohol(s) is generally between about 3 wt % to about 40 wt %, preferably between about 3 wt % to about 20 wt %, more preferably between about 3 wt % to about 10 wt %, and most preferably between about 3 wt % to about 7 wt %, based on the weight of the total composition. In a preferred embodiment of the present disclosure, methanol may be used at concentrations from about 3 wt % to about 7 wt %, based on the weight of the total composition.

As discussed herein, the mixture can include a non-reacting co-solvent. The non-reacting co-solvent can include a compound which is inert to the epoxidation reaction. For example, the non-reacting co-solvent does not take part in the reaction under the reaction conditions, does not react appreciably with the peroxide compound or the oxirane under reaction conditions, is minimally soluble in water, and has a boiling point substantially different than the oxirane to be produced from the epoxidation reaction.

Examples of the non-reacting co-solvent(s) can include, but are not limited to, aliphatic, cycloaliphatic, and aromatic hydrocarbons. Additionally, the non-reacting co-solvent(s) can include, but is not limited to, linear and cyclic alkanes of $C_3$-$C_{18}$, halogenated hydrocarbons, deactivated aromatics, and solvents containing nitriles, e.g., acetonitrile; or mixtures thereof. For example, the non-reacting co-solvent may include, but is not limited to, carbon tetrachloride, propyl chloride, chloroform, dichloromethane, dichloroethane, hexane, octane, decalin, perfluorodecalin, mono- or poly-chlorinated benzenes, mono- or poly-brominated benzenes, acetophenone, benzonitrile, acetonitrile, trichlorotrifluoroethane, trichloroethanol, trifluoroethanol, tricresyl phosphate, or mixtures of two or more of the above-mentioned compounds. For one or more embodiments, the non-reacting co-solvent is 1,2-dichlorobenzene.

In a particularly advantageous embodiment of the present disclosure, the non-reacting co-solvent may be selected from those which have solubility parameters similar to the olefin to be epoxidized, as estimated using Hansen parameters and a Teas plot. Preferred non-reacting co-solvents are chosen from, but are not limited to, those with hydrogen bonding force from about 0.0 to about 0.3, dispersion force from about 0.4 to about 1.0, and polar force from about 0.0 to about 0.5. These solvents will have a high affinity for the olefin to be epoxidized, such as epichlorohydrin, and a low affinity for water, resulting in increased sequestration of the olefin to be epoxidized, such as epichlorohydrin, in the organic phase of the multiphase reaction system.

The concentration of the non-reacting co-solvent is generally between about 5 wt % to about 70 wt %, preferably between about 5 wt % to about 55 wt %, more preferably between about 10 wt % to about 50 wt %, and most preferably between about 10 wt % to about 45 wt %, based on the weight of the total composition.

In a preferred embodiment of the present disclosure, 1,2-dichlorobenzene may be advantageously used as the non-reacting co-solvent in concentrations between about 10 wt % to about 30 wt %, based on the weight of the total composition.

Other optional components, that may be useful in the present disclosure, are components normally used in resin formulations known to those skilled in the art. For example, the optional components may comprise compounds that can be added to the composition to enhance the reaction rate, the selectivity of the reaction, and/or the catalyst lifetime. The preferred optional components and their relative concentrations useful in the composition of the present disclosure can be determined by the skilled artisan.

As an illustration of one embodiment, the present disclosure may be directed to a specific mixture of a small amount (e.g. 3 wt %-7 wt %) of methanol along with a non-reacting co-solvent, with an excess of an olefin compound, such as allyl chloride, such that the olefin is about 40 wt % to 65 wt %, based on the weight of the total composition, making the olefin such as allyl chloride the main solvent. The resulting reaction mixture consists of at least two liquid phases, the solid catalyst, and a vapor phase which is in contact with the other phases or components present in the reaction mixture, which increases the selectivity of the reaction without the need for other additives.

The reaction of an olefin with a peroxide compound such as hydrogen peroxide for the preparation of an oxirane can be carried out in the reaction vessel herein by any suitable method, such as for example, in a batch process or continuously. In one embodiment, the process above may be carried out either in at least one batch reactor or at least one continuous reactor, or any combination of these.

With respect to the continuous processes, a variety of suitable reactor arrangements may be useful in the present disclosure. Thus, for example, the oxirane can be prepared in a cascade of two or more reaction vessels connected to one another in series. Conceivable processes useful in the present disclosure also include for example those in which reaction vessels are arranged in parallel. Combinations of these processes are also possible. In the case where two or more reaction vessels are connected in series, suitable intermediate treatments can also be provided between the reaction vessels.

For example, in a first embodiment of the process according to the present disclosure, the olefin, the peroxide compound, the alcohol(s), the at least one solvent, and the catalyst are fed into at least one reaction vessel, and the resulting liquid phases are removed from the reaction vessel; the solid phase (e.g., catalyst) in the reaction vessel can be separated from the liquid portions of the effluents before the liquid phases are separated in the separation vessel. This operation may be carried out in a batch process or continuously. In this first embodiment, any portion of the reactor effluent may be recycled as a feed to the reaction vessel.

In a second embodiment of the process according to the present disclosure, the olefin, the peroxide compound, the alcohol(s), the at least one solvent, and the solid phase (e.g., catalyst) are fed into at least one reaction vessel, and all of the resulting liquid phases and the solid phase are removed from the reaction vessel and further separated in subsequent operations. This may be carried out in a batch process or continuously. In this second embodiment, any portion of the reactor effluent may be recycled as a feed to the reaction vessel.

In a third embodiment of the process according to the present disclosure, at least two reaction vessels are connected in series. The olefin, the peroxide compound, the alcohol(s), the at least one solvent are fed into a first of the reaction vessels containing the solid phase, and the liquid phases are removed from the reaction vessel; the solid phase in each of the reaction vessels is separated from the liquid portions of the effluents before the liquid phases are separated in the separation vessel. In this third embodiment, all or a portion of the liquid effluent from the first of the reaction vessels may be fed into a subsequent reaction vessel containing the solid phase (e.g., catalyst), and additionally, fresh olefin, peroxide compound, alcohol(s), at least one solvent, and catalyst feeds may optionally be added to each subsequent reaction vessel along with the portions of effluent from any previous reaction vessel.

In a fourth embodiment of the process according to the present disclosure, at least two reaction vessels are connected in series. The olefin, the peroxide compound, the alcohol(s), and the at least one solvent are fed into a first of the reaction vessels containing the solid phase (e.g., catalyst), and the resulting liquid phases and the solid phase are removed from the first of the reaction vessels. The solid phase and the liquid phases are separated in subsequent operations. In this fourth embodiment, all or a portion of the liquid effluent and optionally a portion of the solid phase from the first of the reaction vessels and subsequent reaction vessel(s) may be fed into a subsequent reaction vessel containing the solid phase, and additionally, fresh olefin, peroxide compound, alcohol(s), at least one solvent, and the solid phase feeds may optionally be added to each subsequent reactor along with the portions of effluent from any previous reaction vessel.

In a fifth embodiment of the process according to the present disclosure, two or more reaction vessels are operated in parallel. The olefin, the peroxide compound, the alcohol(s), and the at least one solvent are fed into each reaction vessel containing the solid phase (e.g., catalyst), and the resulting liquid phases are removed from each reaction vessel. In this embodiment of the present disclosure, the solid phase in each reaction vessel is separated from the liquid portions of the effluents before the liquid phases are separated in the separation vessel. In this fifth embodiment of the disclosure a portion of the effluent stream from a reaction vessel may be recycled back to that same reaction vessel along with fresh feeds. The reactor effluents may remain separate or may be combined for further processing.

In a sixth embodiment of the process according to the present disclosure, one or more reaction vessels are operated in parallel. The olefin, the peroxide compound, the alcohol(s), and the at least one solvent are fed into each reaction vessel containing solid phase (e.g., catalyst), and the resulting liquid phases and the solid phase are removed from each reaction vessel. In this embodiment, a portion of the liquid effluent and, optionally, a portion of the solid phase from each reaction vessel may be recycled back to that same reaction vessel along with fresh feeds. In this sixth embodiment, the reactor effluents may remain separate or may be combined for further processing.

In a seventh embodiment of the process according to the present disclosure, at least two reaction vessels are connected in series and the olefin and peroxide compound are fed through the reaction vessels in counter-current flow. The olefin, none or at least a portion of the alcohol(s), the at least one solvent, and the solid phase (e.g., catalyst) are fed into a first of the reaction vessels containing the solid phase (e.g., the catalyst), and the peroxide compound and none or at least a portion of the alcohol(s) are fed into the second of the reaction vessels containing the solid phase or, if more than two reaction vessels, into the final reaction vessel.

The aqueous phase of the effluent of the final reaction vessel and any reaction vessels downstream of the first reaction vessel, containing partially converted peroxide, is separated from both the catalyst phase and the organic phase containing the oxirane, the at least one solvent, and any remaining olefin, and is fed to one or more upstream reaction vessels in the series. The organic phase of the effluent from the first and subsequent reaction vessel(s), containing any unreacted olefin, alcohol(s), at least one solvent, and oxirane, is separated from both the solid phase and the aqueous phase of the effluent and is fed to one or more downstream reaction vessels containing the solid phase in the series. This flow pattern repeats for all reaction vessels in the series. In this seventh embodiment of the present disclosure, the solid phase in each reactor is separated from the liquid portions of the effluents before the liquid phases are separated in the separation vessel.

In an eighth embodiment of the process according to the present disclosure, at least two reaction vessels are connected in series and the olefin and peroxide compound are fed through the reaction vessels in counter-current flow. The olefin, all or a portion of the alcohol(s), the at least one solvent, and the solid phase (e.g., catalyst) are fed into the first reaction vessel containing the solid phase, and the peroxide compound and all or a portion of the alcohol(s) are fed into the second reaction vessel or, if more than two reaction vessels, into the final reaction vessel. The aqueous phase of the effluent of the final reaction vessel and any reaction vessel(s) downstream of the first reaction vessel, containing partially converted peroxide, is separated from both the solid phase and the organic phase containing the oxirane, the at least one solvent, and any remaining olefin, and is fed to one or more upstream reaction vessels containing the solid phase in the series. The organic phase of the effluent from the first and subsequent reaction vessel(s), containing any unreacted olefin, alcohol(s), at least one solvent, and oxirane, is separated from both the solid phase and the aqueous phase of the effluent and is fed to one or more downstream reaction vessels containing the solid phase in the series. This flow pattern repeats for all reaction vessels in the series. In this eighth embodiment of the present disclosure, the solid phase in each reaction vessel is separated from the liquid portions of the effluents in one or more separate operation(s).

In a ninth embodiment of the process according to the present disclosure, at least two reaction vessels are connected in series and the olefin and peroxide compound are fed through the reaction vessels in cross-current flow. The solid phase, the first portion of olefin, a portion of the alcohol(s), the at least one solvent, and all of the peroxide compound are introduced into a first of the reaction vessels containing the solid phase, an epoxidation of the first portion of the olefin is carried out therein in order to form a first portion of the oxirane. The liquid phases of the effluent of this and subsequent reaction vessel(s) are first separated from the solid phase, and the organic phase of the first of the reaction vessels containing unreacted olefin, alcohol(s), at least one solvent, and oxirane generated is fed into at least one subsequent reaction vessel containing the solid phase, to which fresh peroxide compound feed is introduced. This flow pattern is repeated for all reaction vessels in the series. The solid phase (e.g., catalyst) is separated from the final reactor effluent before the two liquid phases are separated in the separation vessel.

In a tenth embodiment of the process according to the present disclosure, at least two reaction vessels are connected in series and the olefin and peroxide compound are fed through the reaction vessels in cross-current flow. The first portion of olefin, a portion of the alcohol(s), the at least one solvent, and all of the peroxide compound are introduced into a first of the reaction vessels containing the solid phase (e.g., catalyst), an epoxidation of the first portion of the olefin is carried out therein in order to form a first portion of the oxirane. The liquid phases of the effluent of this reaction vessel are discharged along with the solid phase, and the solid phase is separated from the liquid phases in subsequent operations. The organic phase of the first and subsequent reaction vessels containing unreacted olefin, alcohol(s), at least one solvent, and oxirane generated is fed into at least one subsequent reaction vessels containing the solid phase, to which fresh peroxide compound feed and solid phase are introduced. This flow pattern is repeated for all reaction vessel(s) in the series. The solid phase can be separated from the final reaction vessel effluent liquid phases in subsequent operations.

In an eleventh embodiment of the process according to the present disclosure, at least two reaction vessels are connected in series and the olefin and peroxide compound are fed through the reaction vessels in cross-current flow. The first portion of olefin, a portion of the alcohol(s), the at least one solvent, and all of the peroxide compound are introduced into a first of the reaction vessels containing the solid phase (e.g., catalyst), an epoxidation of the first portion of the olefin is carried out therein in order to form a first portion of the oxirane. The liquid phases of the effluent of this reaction vessel are first separated from the solid phase, and the aqueous phase of the first and subsequent reaction vessel(s) containing unreacted peroxide compound is fed into at least one subsequent reaction vessel containing the solid phase, to which fresh olefin, alcohol(s), at least one solvent and the solid phase are introduced. This flow pattern is repeated for the reaction vessels in the series. The solid phase can be separated from the final reaction vessel effluent before the two liquid phases are separated.

In a twelfth embodiment of the process according to the present disclosure, at least two reaction vessels are connected in series and the olefin and peroxide compound are fed through the reaction vessels in cross-current flow. The first portion of olefin, a portion of the alcohol(s), the at least one solvent, and all of the peroxide compound are introduced into a first of the reaction vessels containing the solid phase (e.g., catalyst), an epoxidation of the first portion of the olefin is carried out therein in order to form a first portion of the oxirane. The liquid phases of the effluent of this reaction vessel are discharged along with the solid phase, and the solid phase is separated from the liquid phases in subsequent operations. The aqueous phase of the first and subsequent reaction vessels containing unreacted peroxide compound is fed into at least one subsequent reaction vessel containing the solid phase, to which fresh olefin, alcohol(s), at least one solvent and the solid phase are introduced. The solid phase can be separated from the final reaction vessel effluent liquid phases in subsequent operations.

The temperature and pressure of the reaction medium can be modified during the process in the course of the preparation of the oxirane from an olefin and a peroxide compound. The pH and temperature of the reaction medium can likewise be modified. It is furthermore possible, in addition to the pH and temperature of the reaction medium, additionally to modify the pressure under which the reaction takes place.

In one preferred embodiment, the process of the present disclosure produces an aqueous waste stream with little, or no significant amount of, sodium chloride (NaCl). By "no significant amount" with reference to the sodium chloride it is meant herein as generally less than about 1 wt %, preferably less than about 0.5 wt %, and most preferably less than about 0.1%, based on the weight of the total composition.

In another embodiment of the process of the present disclosure, the reaction environment may include a vapor phase in contact with the multiple liquid phase composition. Following the reaction, the resulting two liquid phases formed during the reaction in the reaction mixture, a liquid organic phase and a liquid aqueous phase, may be separated from each other and from the solid phase. Each liquid phase may then be separated into smaller components for recycle, product recovery, or purge stream isolation. Unreacted olefin, alcohol(s), and non-reactive solvent(s) may be returned to the reaction vessel(s); and water and byproducts may be purged from the process.

In still another embodiment, the process of the present disclosure may include immediately separating the water from the reaction product to minimize the contact of these compounds in the high temperature sections of the separation section and thus minimize the formation of by-products.

In a specific embodiment of the present disclosure, a process for preparing an oxirane includes the steps of: (a) reacting an olefin, wherein the olefin is selected from one of (i) an aliphatic olefin or substituted aliphatic olefin, (ii) a cycloaliphatic olefin, (iii) an aromatic olefin, (iv) a cycloaromatic olefin, and (v) mixtures thereof; a solid phase (e.g., catalyst), a peroxide compound, an alcohol or a mixture of alcohols, and a non-reacting co-solvent together to form a reaction mixture; wherein the reaction mixture contents comprise at least two liquid phases and the solid phase; and decanting the reaction mixture contents; wherein the liquid phases are separated from the solid phase; and wherein the liquid phases are recovered for further processing; (b) separating the two liquid phases, recovered from step (a) from each other to form a liquid aqueous phase and a liquid organic phase; (c) separating, in at least one separation unit operation, organic compounds present in the liquid aqueous phase of step (b), from the liquid aqueous phase to form an organic compounds stream and a wastewater stream; (d) recycling the organic compounds stream of step (c) to the reaction mixture; and recovering or sending the wastewater stream of step (c) to a subsequent processing operation; (e) recovering, in at least one operation unit, the organic phase of step (b) comprising the non-reacting co-solvent, unreacted olefin, and the oxirane; (f) separating the oxirane from the other components of the organic phase; (g) recovering the oxirane product from step (f); (h) recycling the unreacted olefin and the non-reacting co-solvent stream of step (f) to the reaction mixture; and (i) optionally, purging any undesired compounds which build up in the recycle streams.

Step (a) of the above process may be referred to as a "reaction/decanting step."

In a preferred embodiment, the oxirane, such as epichlorohydrin, may be prepared by a process comprising reacting (a) an olefin, such as allyl chloride, with (b) a peroxide compound, such as hydrogen peroxide, in the presence of (c) a catalyst, such as titanium silicalite-1 (TS-1), and (d) in the presence of a solvent mixture; wherein the solvent mixture comprises at least (i) one or more alcohols, such as methanol, and (ii) at least one non-reacting co-solvent.

In the process of the present disclosure, the reaction of the olefin such as an allyl chloride with the peroxide compound such as hydrogen peroxide takes place in one or more reaction vessels, as discussed herein. The preferred starting materials used for the reaction of the present disclosure may be fed into the reaction vessel in one or more streams. For example, the streams are fed in liquid form into the reaction vessel to form a multiphasic or at least a biphasic system. In the process of the present disclosure, preference is given to feeding streams consisting of the combination of the aqueous starting materials and streams consisting of the combination of the organic starting materials into the reaction vessel.

It is possible to use a variety of reaction vessels known in the art. In the present disclosure, the term "reactor" or "reaction vessel" is not restricted to a single vessel. Rather, it is also possible to use two or more stirred reaction vessels as the reaction vessel such as described herein.

The reaction vessel may comprise a variety of well-known reactor types, including for example, one or more continuous stirred tank reaction vessels (CSTRs), batch reaction vessels or tubular reaction vessels; or combinations thereof. The reactor may comprise other known liquid-liquid contactors, such as for example a Karr Column. For the reaction step, sufficient mixing may be required to ensure that the olefin, the peroxide compound and the solid phase come into intimate contact. The mixing may comprise known means for mixing such as, for example, but are not limited to, stirring with an agitator, by controlling droplet size in a countercurrent extractor, by inducing shear with a mixing element in a tubular reactor or loop reactor, or by other means. Mixing intensity should be such that the power/volume input to the reactor is preferably 1 to 100 hp/1000 gal, more preferably 1 to 10 hp/1000 gal and most preferably 2 to 4 hp/1000 gal. Interfacial area needs to be sufficiently-high-enough to allow sufficient mass transfer to occur for reaction to occur.

Once the solid phase (e.g., catalyst) is separated from the liquid reaction phases, the multiple reaction phases facilitate the subsequent recovery of oxirane product, such as epichlorohydrin, by allowing a separation of the liquid aqueous and liquid organic phases by, for example, decantation, prior to recovery of recyclable and useful product components from each stream. In one or more embodiments, the separation of the liquid aqueous and liquid organic phases can occur in a separation vessel. See for example FIGS. 1-4. By reducing the amount of methanol to a predetermined level, which is lower than the levels used in the prior art processes, the selectivity of the reaction to oxirane product may be increased because the reaction of methanol with oxirane product is reduced. When the methanol is reduced, a reaction mixture of at least two liquid phases results, which is advantageous because the majority of the oxirane product remains in the organic phase, which reduces byproducts, for example 1-chloro-3-methoxy-2 propanol, 1-chloro-2-methoxy-3-propanol, and 1-chloro-2,3-propanediol, formed from the reaction of oxirane product with water and methanol. Also, many of the heavy byproducts formed remain in the aqueous phase. It is a critical element of the reaction that the reaction remains in at least two liquid phases so that the oxirane product formed will be sequestered away from the aqueous phase and into one of the organic phases. This greatly reduces the hydrolysis of the oxirane product to by-products.

The reaction may be carried out in a mixed solvent system consisting of a small amount of methanol with a non-reacting co-solvent. The advantages that the system of the present disclosure offers are increased catalyst lifetime and decreased energy costs for separation. For example, based on a simulation of the process taught by U.S. Pat. No. 6,288,248 B1 the embodiment presented in FIG. 3 results in a reduction of about 35% in energy required per pound of oxirane product produced. The embodiment presented in FIG. 4 results in a reduction in steam usage and the embodiment presented in FIG. 4 represents an energy reduction of about 55% from the process of the prior art. The presence of methanol in the reactor at a concentration of generally between about 3 wt % to about 40 wt %, preferably between about 3 wt % to about 20 wt %, more preferably between about 3% to about 10%, and most preferably between about 3 wt % to about 7 wt %, based on the weight of the total composition, extends catalyst lifetime as described in the examples.

Another advantage of the present disclosure is that the addition of the non-reacting co-solvent(s) increases the catalyst lifetime by reducing the plugging of the catalyst pores.

Still another advantage of the present disclosure is that the biphasic nature of the reaction mixture allows the separation of the liquid organic phase and the liquid aqueous phase by decanting, which reduces the size of distillation towers and the steam consumption, compared to a process that would use a high level of methanol.

It has been discovered that TS-1 catalyst activity in the epoxidation of an olefin such as allyl chloride with a peroxide compound such as $H_2O_2$ can be maintained by using a mixture of solvents comprising less than 10 wt % methanol along with a non-reactive co-solvent. At a temperature of 40° C. and atmospheric pressure, this mixture provides better reuse of the catalyst while also facilitating the separation of oxirane product such as epichlorohydrin from the reaction mix.

The process of the present disclosure may be carried out at a reaction temperature generally in the range of from about 10° C. to about 100° C., preferably from about 20° C. to about 80° C., and more preferably from about 30° C. to about 50° C. The other conditions of running the process of the present disclosure, such as pressure would be the relative pressure and other conditions of the reaction associated with the reactor composition at the particular temperature. However, as an illustration, the reaction may be carried out at pressures in the range from 1 bar to 30 bar, preferably from 1 bar to 20 bar and particularly preferably from 1 bar to 15 bar.

For one or more embodiments, the system and process of the present disclosure includes allowing the mixture to separate into the liquid aqueous phase and the liquid organic phase. The liquid aqueous phase and the liquid organic phase can be two immiscible liquids that form an immiscible fluid interface. Allowing the mixture to separate into the liquid aqueous phase and the liquid organic phase can include allowing the mixture to settle in a separation vessel, as discussed herein. The liquid organic phase can have a density greater than the liquid aqueous phase. As such, the liquid organic phase settles below the liquid aqueous phase, which has a density that is less than the liquid organic phase. In other words, the liquid organic phase is a bottom layer in the vessel and the liquid aqueous phase is a top layer in the separation vessel.

As discussed herein, the mixture can be the reaction mixture from the epoxidation reaction between the olefin and the peroxide compound. The reaction mixture can include the olefin, the peroxide compound, water, the oxirane, the alcohol mixture, the non-reactive solvent, and the solid phase. For example, the reaction mixture can include allyl chloride, hydrogen peroxide, water, epichlorohydrin, methanol, 1,2-dichlorobenzene, and the TS-1 catalyst. For one or more embodiments, allowing the mixture to settle in the separation vessel can include agitating the mixture. Agitating the mixture can assist in separating the solid phase from the liquid organic phase. Agitation can be performed by known means for agitating, such as, but not limited to, stirring with an agitator or by inducing shear with a mixing element in the separation vessel. For the embodiments, the agitation is performed such that the immiscible fluid interface between the liquid aqueous phase and the liquid organic phase is maintained within the vessel.

For one or more embodiments, a first part of the solid phase remains suspended in the liquid aqueous phase in the separation vessel. The first part of the solid phase can remain suspended in the liquid aqueous phase because of the affinity of the solid phase for the liquid aqueous phase. For one or more embodiments, the first part of the solid phase is greater than 50 wt %, preferably greater than 75 wt %, more preferably greater than 95 wt %, and still more preferably greater than 98 wt %, based on a total weight of the solid phase.

For one or more embodiments a second part of the solid phase can settle through the liquid organic phase to a density driven position. While the solid phase has an affinity for the liquid aqueous phase, an amount of the solid phase will not remain suspended in the liquid aqueous phase because its surface has been modified. As discussed herein, the solid phase has a density greater than both the liquid aqueous phase and the liquid organic phase. Therefore, the second part of the solid phase that does not remain suspended in the liquid aqueous phase can settle at least partially through the liquid organic phase to a density driven position. For one or more embodiments, the second part of the solid phase is less than 50 wt %, preferably less than 25 wt %, more preferably less than 5 wt %, and still more preferably less than 2 wt %, based on a total weight of the solid phase.

For one or more embodiments, the process includes recovering the liquid organic phase. Recovering the liquid organic phase can include removing the liquid organic phase from a point within a volume of the liquid organic phase in the separation vessel. For one or more embodiments, the liquid organic phase recovered from the separation vessel can contain less than 1 wt % of the solid phase. In one embodiment, the liquid organic phase contains zero (0) wt % of the solid phase. For one or more embodiments, recovering the liquid organic phase from the vessel can be performed by known techniques for removing a liquid from a vessel. Examples can include, but are not limited to, an outlet port, an overflow port, a pressure differential, pumping such as any pump capable of handling a solid slurry, and combinations thereof.

The liquid organic phase removed from the separation vessel can include water, the second part of the solid phase, oxirane, olefin, alcohol mixture, and non-reacting co-solvent (s). The liquid organic phase removed from the separation vessel can contain a majority of the oxirane formed during the epoxidation reaction, e.g., more than 50 wt %, based on a total weight of the oxirane produced. The liquid organic phase removed from the separation vessel can undergo further processing to recover the oxirane and separate and recycle the olefin, the alcohol mixture, and the non-reactive solvent(s).

For one or more embodiments, the system and process includes recovering the liquid aqueous phase that includes the first part of the solid phase. Recovering the liquid organic phase from the separation vessel can be performed by known techniques for removing a liquid from a vessel. Examples can include, but are not limited to, an outlet port, an overflow port, a pressure differential, pumping such as any pump capable of handling a solid slurry, and combinations thereof. In one embodiment, the liquid aqueous phase is removed from a liquid aqueous phase overflow port of the separation vessel. The liquid aqueous phase can include the first part of the solid phase, water, peroxide compound, oxirane, olefin, and alcohol mixture. The liquid aqueous phase includes a majority of water, the peroxide compound and the alcohol mixture present in the reaction mixture. However, the liquid aqueous phase can include a portion of the oxirane and the olefin. For one embodiment, the oxirane and the olefin can be less than 5 wt %, based on the total weight of the liquid aqueous phase.

For one or more embodiments, the system and process includes extracting at least the oxirane from the liquid aqueous phase with an extraction solvent. For one or more embodiments, the process can further include extracting the olefin from the liquid aqueous phase with the extraction solvent. For the present disclosure, extracting the oxirane and the olefin can prevent destruction of the oxirane and the olefin present in the liquid aqueous phase. For example, the liquid aqueous phase could be sent to a digest reactor to deplete the peroxide compound to acceptable levels before the liquid aqueous phase is sent to a distillation unit operation. However, if the oxirane and olefin are not extracted from the liquid aqueous phase prior to the digest reactor, the oxirane and olefin can be destroyed during the digestion of the peroxide compound. The oxirane and the olefin could also be destroyed in a distillation unit.

Eliminating the oxirane can decrease the profitability of the process since the portion of the product is being eliminated versus being sold. Additionally, eliminating the olefin that has not reacted with the peroxide compound during the epoxidation reaction can increase the cost of producing the oxirane since the olefin is not reacting to form the oxirane. Thus, extracting the oxirane from the liquid aqueous phase can help increase the efficiency of the epoxidation reaction since more of the oxirane will be recovered. Moreover, extracting the olefin can reduce costs associated with producing the oxirane by not eliminating starting materials and thereby minimizing the amount of olefin used to produce the oxirane.

For one or more embodiments, the liquid aqueous phase can be separated from the first part of the solid phase before the oxirane and the olefin are extracted using the extraction solvent. Separating the first part of the solid phase from the liquid aqueous phase can be performed by known separation techniques including, but not limited to, hydrocyclone, filtration, centrifugation, and gravity. Alternatively, the oxirane and olefin can be extracted from the liquid aqueous phase without having to separate the liquid aqueous phase from the first part of the solid phase.

For one or more embodiments, the extraction solvent can be selected from solvents that are present in the process for producing the oxirane. For example, the extraction solvent used in the present disclosure can be the non-reactive co-solvent. In one embodiment, the extraction solvent is different than the olefin used in the process for producing the oxirane. In one embodiment, the extraction solvent and/or the non-reactive co-solvent can be 1,2-dichlorobenzene. Additionally, the extraction solvent used does not increase an amount of the olefin in the liquid aqueous phase. Additional extraction solvents may include, but not be limited to, isopropyl chloride, n-propyl chloride, and tricresyl phosphate.

For one or more embodiments, extracting the oxirane and olefin is done from only the liquid aqueous phase. Extracting the oxirane and olefin from only the liquid aqueous phase can reduce an amount of extraction solvent used as compared to an amount of extraction solvent that would be used to extract the oxirane and olefin from both the liquid aqueous phase and the liquid organic phase. Reducing the amount of the extraction solvent used can lower a unit ratio of extraction solvent needed for the production of the oxirane. That is, extracting from only the liquid aqueous phase reduces the amount of extraction solvent used for producing the same amount of oxirane as a process that extracts from both the liquid aqueous and liquid organic phase. Additionally, the reduced amount of extraction solvent is such that, unlike previous approaches, it is not cost or energy prohibitive to send the extraction solvent to distillation, rather than to the reactor; consequently, increasing the efficiency and production of the process.

The process of the present disclosure does not require the olefin in the liquid aqueous phase to be recovered or destroyed. For example, using an extraction solvent that is used in the epoxidation reaction allows for the extraction solvent that has been used to extract the olefin from the liquid aqueous phase to be recycled to the reaction vessel of the epoxidation reaction. This helps to minimize the throughput of the extraction solvent, which can decrease the cost of solvent recovery operations. For example, increasing the throughput of extraction solvent can increase the solvent recovery costs since the extraction solvent would be distilled prior to recycle to a reactor.

For one or more of the embodiments, the reaction mixture can include other optional compounds that may be useful in the present disclosure. For example, optional compounds that can enhance a reaction rate, a selectivity of the epoxidation reaction, and/or the solid phase catalyst phase lifetime can be included. The preferred optional components and their relative concentrations useful in the composition of the present disclosure can be determined by the skilled artisan.

As discussed herein, embodiments of the present disclosure provide a process for preparing an oxirane. As discussed herein, the reaction mixture includes the liquid aqueous phase and the liquid organic phase, where the liquid organic phase can have a density greater than the liquid aqueous phase and the solid phase catalyst can have a density greater than the liquid organic phase. Surprisingly, it has been found that a solid phase (e.g., catalyst) according to the present disclosure has an affinity for the liquid aqueous phase and can remain in the liquid aqueous phase even when the liquid aqueous phase has a density lighter than the liquid organic phase and the solid phase has a density greater than both the liquid aqueous phase and the liquid organic phase. This affinity of the solid phase for the liquid aqueous phase can allow for non-mechanical separation techniques of the mixture, e.g., gravity decantation.

Embodiments of the present disclosure, therefore, further provide a process for separating phases of the reaction mixture. The process may include receiving the reaction mixture including the liquid aqueous phase, the liquid organic phase including the oxirane, and the solid phase. The liquid organic phase can have a density greater than the liquid aqueous phase and the solid phase can have a density greater than the liquid organic phase. For one or more embodiments, the solid phase can have an affinity for the liquid aqueous phase. The affinity of the solid phase for the liquid aqueous phase can allow a first part of the solid phase to remain suspended in the liquid aqueous phase.

For one or more embodiments, the process can include (b) separating the reaction mixture into the liquid aqueous phase and the liquid organic phase to separate the solid phase catalyst from the liquid organic phase. The liquid organic phase can settles beneath the liquid aqueous phase due to the density difference. However, a first part of the solid phase catalyst remains with and suspends within the liquid aqueous phase, e.g., the upper layer, irrespective of the density difference because of the affinity of the solid phase catalyst for the liquid aqueous phase. The liquid aqueous phase includes the first part of the solid phase and the liquid organic phase can include the second portion of the solid phase catalyst that has settled through the liquid organic phase to the density driven position.

For one or more embodiments, the process can include (c) recovering, in at least one operation unit, the liquid organic phase of step (b) including the non-reactive solvent, the olefin, and the oxirane, as discussed herein.

For one or more embodiments, the process can include (d) recovering, in at least one operation unit, the liquid aqueous phase of step (b) including the first part of the solid phase catalyst, and (e) extracting, in at least one separation unit operation, organic compounds present in the liquid aqueous phase of step (d) from the liquid aqueous phase with an extraction solvent. For one or more embodiments, the organic compounds include the oxirane and the olefin. The extraction solvent can be selected from the extraction solvents as discussed herein.

For one or more embodiments of the present disclosure, the process can further include (f) separating the oxirane from the liquid organic phase, (g) recovering the oxirane product from step (f), and (h) recycling a remaining amount of the olefin and the alcohol mixture and the non-reactive solvent(s) stream of step (g) back to the reaction mixture.

FIG. 1 illustrates a separation vessel 102 and a reaction vessel 106 used in the system and process according to an embodiment of the present disclosure. Stream 104 is the mixture including the liquid aqueous phase, the liquid organic phase, and the solid phase. The separation vessel 102 can receive stream 104 from a reaction vessel 106. As discussed herein, the mixture can be the reaction mixture from the epoxidation reaction to form the oxirane. For example, stream 104 can be the reaction mixture from the epoxidation reaction and include the olefin, the peroxide compound, the solid phase catalyst, the alcohol mixture, the non-reactive solvent, and the oxirane. For one or more embodiments, the separation vessel 102 can also be used as the reaction vessel to form the oxirane.

For one or more embodiments, the mixture is allowed to separate in separation vessel 102. For example, the liquid aqueous phase can separate from the liquid organic phase and the solid phase can suspend within the liquid aqueous phase. As discussed herein, the liquid aqueous phase can include the first part of the solid phase catalyst and the liquid organic phase can include the second part of the solid phase catalyst that settles through the liquid organic phase to the density driven position. The separation vessel 102 may be selected from known separation vessels, including, but not limited to, decanters, hydrocyclones, mechanically driven high gravity devices, or other separation apparatus known in the art. In one embodiment, the separation vessel 102 is a gravity decanter.

For one or more embodiments, stream 108 contains the liquid aqueous phase including the first part of the solid phase. The liquid aqueous phase can be removed from the separation vessel 102 by allowing the liquid aqueous phase to overflow from a liquid aqueous phase overflow port 110 of separation vessel 102. The contents of stream 108 can include water, the first part of the solid phase catalyst, peroxide compound, olefin, oxirane, and alcohol mixture. Stream 108 can be transported to further processes and/or unit operations, as discussed herein, such as extraction, regeneration, centrifugation, distillation, and combinations of these to recover the catalyst, oxirane, and the alcohol mixture.

Stream 112 contains the liquid organic phase including the second part of the solid phase. The contents of stream 112 can include the second part of the solid phase catalyst, oxirane, olefin, alcohol mixture, and non-reactive solvent(s).

Stream 112 can be transported to further processes and/or unit operations. For example, stream 112 can be filtered or centrifuged to remove the second part of the solid phase from the liquid organic phase or sent to distillation towers to recover the oxirane and separate and recycle other compounds of the liquid organic phase, e.g., the olefin, the alcohol mixture, and the non-reactive solvent(s).

For one or more embodiments, separation vessel 102 can have a drain valve 114 to periodically drain a portion of the liquid organic phase to remove at least a portion of the second part of the solid phase that has settled to a density driven position. Stream 116 includes the drained liquid organic phase that contains the second part of the solid phase. For one or more embodiments, stream 116 can be filtered to separate the solid catalyst phase from the liquid organic phase.

In one or more embodiments, stream 116 can be recycled back to stream 104. Additionally, stream 116 can be recycled back to the separation vessel 102. As seen in FIG. 1, stream 116 can be connected to stream 104 and/or to separation vessel 102 such that a portion of stream 116 can be recycled to stream 104 and/or a portion can of stream 116 can be recycled to the separation vessel 102. Recycling stream 116 to stream 104 allows the liquid organic phase drained from separation vessel 102 to repeat the separation process. In one or more embodiments, a portion of stream 116 does not get recycled and can be transported to further processes and/or unit operations.

Figure 2:
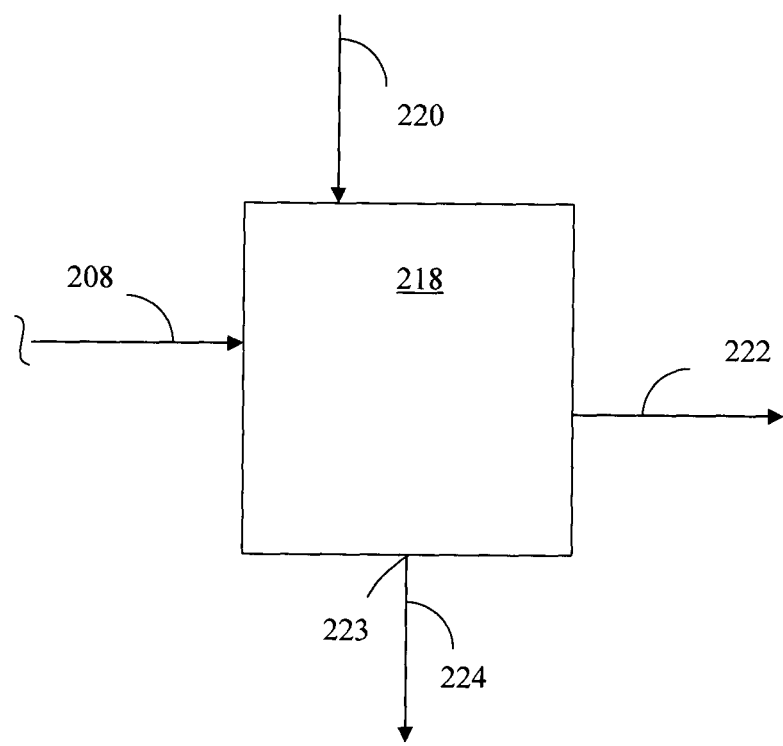
FIG. 2 illustrates an extraction vessel for use with a system and process according to an embodiment of the present disclosure.

FIG. 2 illustrates an extraction vessel 218 used in the system and process according to an embodiment of the present disclosure. The extraction vessel 218 can include an extraction unit operation in which a suitable extraction solvent or mixture of extraction solvents, introduced in stream 220, can be mixed with stream 208. As discussed herein, stream 208 can be filtered or centrifuged prior to entering the extraction vessel 218 to remove the first portion of the solid phase catalyst from the liquid aqueous phase. In at least one embodiment, the first portion of the solid phase may remain in stream 208.

Stream 220 can include one or more extraction solvents, as discussed herein. Stream 208 from the separation vessel (element 102 in FIG. 1) can be mixed with stream 220 in the extraction vessel 218 to extract the oxirane and the olefin from the other components of the liquid aqueous phase. For example, the oxirane and the olefin can be extracted from the other components including, the peroxide compound, water, and the alcohol mixture. As seen in FIG. 2, stream 222 can remove the other components such as the peroxide compound, water, and alcohol mixture from the extraction vessel 218. Stream 222 can be sent to storage, for further processing such as regeneration, purification, and/or disposal. For example, stream 222 can be sent to the digest reactor (not shown), where the peroxide compound is digested to acceptable limits prior to further processing.

For the various embodiments, the extraction vessel 218 includes a first outlet 223 through which stream 224 can exit the extraction vessel 218. Stream 218 can include the extraction solvent(s) plus the oxirane and the olefin. For one or more embodiments, stream 224 can be recycled back to the reaction mixture in the reaction vessel (106 in FIG. 1) to allow the olefin to react in the epoxidation reaction and to recirculate the oxirane. As discussed herein, extracting the oxirane and the olefin from the liquid aqueous phase can reduce an amount of starting materials, e.g., the olefin, and products, e.g., the oxirane that are disposed of during the process for producing the oxirane.

Figure 3:
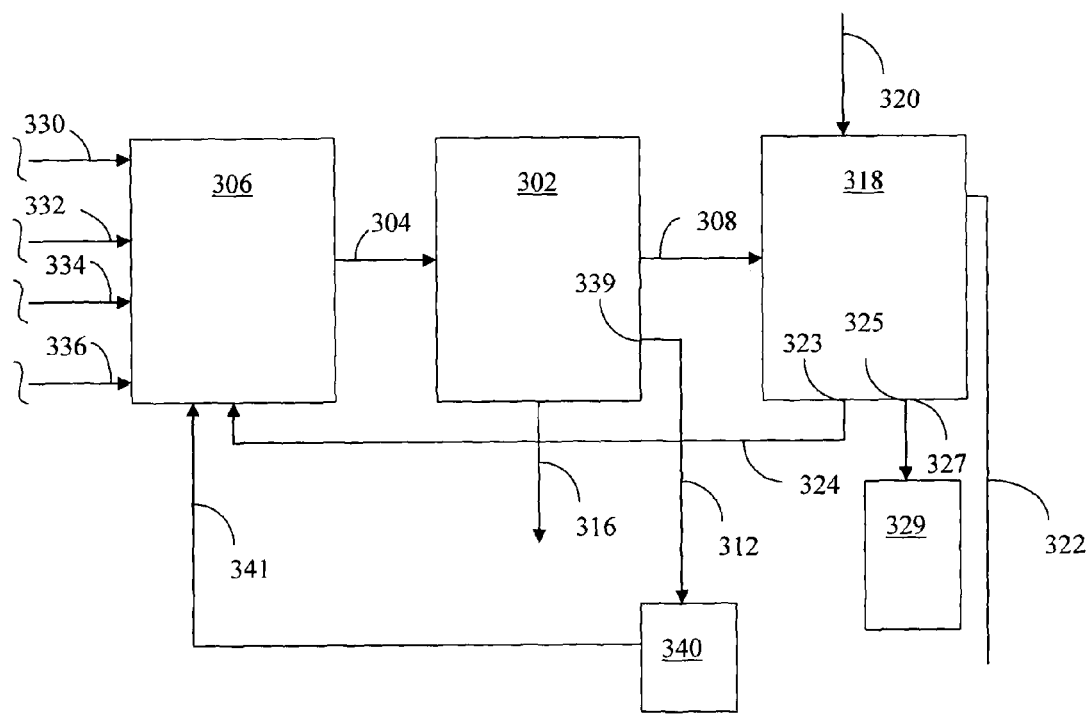
FIG. 3 illustrates a combination of vessels used in (or with) a system and a process according to an embodiment of the present disclosure.
Figure 4:
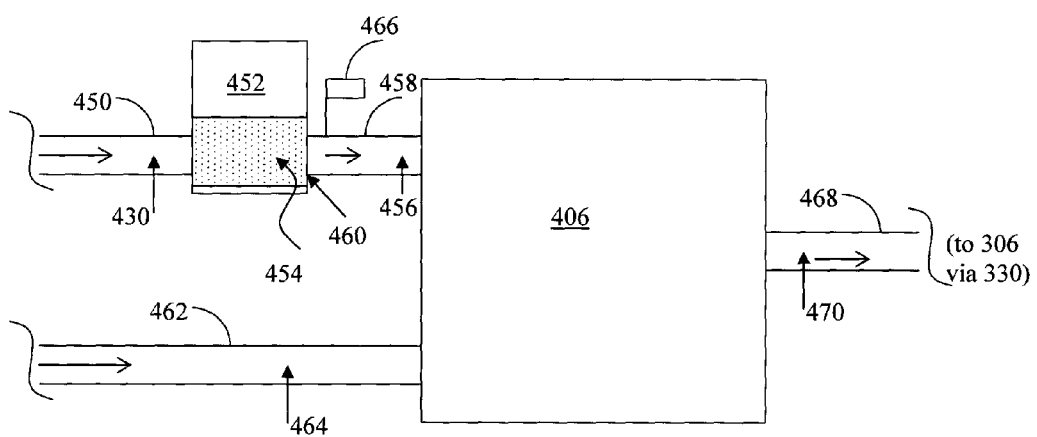
FIG. 4 illustrates an exchange vessel for use with a system and process according to an embodiment of the present disclosure.

FIG. 3 illustrates an embodiment of a system 300 according to the present disclosure. The system 300 includes a combination of the reaction vessel 306 coupled to the separation vessel 302, which is coupled to the extraction vessel 318, all of which are used in a process according to an embodiment of the present disclosure. For one or more embodiments, organic stream 330 and streams 332, 334, and 336 can be fed to the reaction vessel 306 to form the reaction mixture. The reaction vessel 306 can be selected from one or more continuous stirred tank reactors (CSTRs), tubular reactors, fixed-bed reactors, batch reactors, or combinations thereof. When the reaction vessel 306 is a fixed bed reactor, the solid phase (e.g., catalyst) is contained with a fixed bed structure such that the solid phase does not leave the reaction vessel 306 with either of the liquid aqueous phase or the liquid organic phase.

Organic stream 330 can include the olefin, such as an allyl chloride feed stream. Stream 332 can include the peroxide compound, such as a hydrogen peroxide solution. Stream 334 can include a single or mixed alcohols feed stream. Additionally, stream 336 can include the non-reactive solvent(s). For one or more embodiments, the reaction vessel 306 includes the solid phase catalyst, such as a TS-1 catalyst, in either a slurry with the reaction mixture in the reaction vessel 306 and/or in a fixed bed within the reaction vessel 306, where the solid phase remains within the boundaries of the reaction vessel 306.

For one or more embodiments, streams 330, 332, 334, and 336 can be introduced into the reaction vessel 306 either separately or together. Additionally, streams 330, 332, 334, and 336 may be combined together into one feed stream prior to being introduced into the reaction vessel 306. Streams 330, 332, 334, and 336 may be introduced at a single point or at multiple points of the reaction vessel 306. The relative amounts of streams 330, 332, 334, and 336 can be chosen such that when they are combined in the reaction vessel 306 a separate liquid aqueous phase exists along with one or more liquid organic phases, the solid phase catalyst phase, and optionally a vapor phase above the reaction mixture.

For one or more embodiments, the separation vessel 302 coupled to the reaction vessel 306 can receive the reaction mixture in stream 304. In one embodiment, stream 304 can include the liquid aqueous phase including the oxirane, the liquid organic phase, and the solid phase catalyst, as discussed herein. In an alternative embodiment, if a fixed bed reactor is used for the reaction vessel 302, stream 304 can include the liquid aqueous phase including the oxirane and the liquid organic phase, but without the solid phase as this is retained in the fixed bed.

Separation vessel 302 can be selected from a number of separation vessels, as discussed herein with respect to FIG. 1. In one embodiment, separation vessel 302 is a gravity decanter. Stream 312 including the liquid organic phase may be removed from separation vessel 302 and can be sent for further processing, as discussed herein. Additionally, stream 316, including the drained liquid organic phase and the solid phase catalyst (if present), can be recycled back to stream 304 or to the separation vessel 302, as discussed in reference to FIG. 1.

As seen in FIG. 3, the extraction vessel 318 can receive stream 308 from separation vessel 302. As discussed herein, the extraction vessel 318 can include the extraction unit operation in which the extraction solvent or mixture of extraction solvents as stream 320 is mixed with stream 308. Extraction vessel 318 includes a first outlet 323 through which the extraction solvent plus the oxirane and olefin can be recycled back to the reaction-mixture in reaction vessel 306 via stream 324, as discussed herein with reference to FIG. 2. Additionally, the extraction vessel 318 can include a second outlet 325 through which the extraction solvent with the oxirane is transported to a distillation unit operation 329 for separation. In one or more embodiments, stream 322 can proceed to regeneration of the catalyst it contains, recovery and recycle of the catalyst, recovery and recycle of the alcohol mixture, and further processing, as discussed herein. As one skilled in the art can appreciate the recovery of the solid catalyst can be accomplished by a variety of unit operations, such as centrifugation or filtration, for example.

In an additional embodiment, the separation vessel 302 can further include a second outlet 339 to remove the liquid organic phase from the separation vessel 302 via stream 312. As illustrated, the second outlet 339 is coupled to a distillation unit operation 340 via stream 312. The distillation unit operation 340 allows for the separation of oxirane from a remainder of the liquid organic phase, where the remainder of the liquid organic phase can be returned to the reaction mixture in the reaction vessel 306 via stream 341.

Embodiments of the present disclosure also include a system and a process for removing iron ions from the organic stream (330 in FIG. 3) used in the process to form the oxirane. The iron ions are removed from the organic stream prior to contacting the organic stream with the peroxide solution. For one or more embodiments, the iron ions can be removed by contacting the organic stream with an ion exchange resin.

As discussed herein, one process for producing oxiranes includes reacting the olefin, such as allyl chloride, with the peroxide solution. One issue recognized by the present disclosure is that an organic stream containing allyl chloride and more than 50 parts per million of water by weight (also referred to herein as "wet allyl chloride") can be corrosive to ferrous metals. When piping of ferrous metal is used to transport wet allyl chloride during the production of oxirane, the wet allyl chloride can remove iron as ionic iron, i.e., iron ions, from the piping due to this corrosive property. For example, the wet allyl chloride can remove (e.g., dissolve) iron as the organic stream comes into contact with ferrous metal based materials, e.g., in ferrous metal piping material or vessels.

It is also understood that peroxide solutions can be unstable to the point of decomposing spontaneously to water and oxygen gas. As such, stabilizers are added to the peroxide solution to reduce and/or prevent its decomposition. When the organic stream contacts a peroxide solution that includes such stabilizers, the iron ions and stabilizers can form a precipitate, i.e., a by-product. This precipitate can cause problems during the production of the oxirane, as discussed herein. As such, removing and/or reducing the iron ions in the organic stream before contacting the organic stream with the peroxide solution that includes the stabilizer can reduce an amount of by-products, i.e., the precipitate, formed during the production of the oxirane.

For one or more embodiments, the process includes providing the organic stream having iron ions. For example, the organic stream can be an organic stream including the olefin that can be used to make the oxirane. For one or more embodiments, the olefin is allyl chloride. The organic stream can also include additional olefins, as provided herein.

As discussed herein, the water in wet allyl chloride can react with the allyl chloride to form hydrochloric acid, thereby becoming corrosive to equipment containing iron, such as piping, with which it comes into contact. The corrosive activity of the hydrochloric acid can dissolve iron as ionic iron, i.e., iron ions, from the piping and incorporates it into the wet allyl chloride. This corrosive activity helps to form the organic stream, as discussed herein, which contains both the wet allyl chloride and the iron ions. When the iron ions come into contact with stabilizers in the peroxide solution, a precipitate, i.e., a by-product, can form. As discussed herein, minimizing by-products such as precipitates can increase the efficiency of the production of oxiranes, such as the production of epichlorohydrin from the epoxidation reaction of allyl chloride and hydrogen peroxide.

Embodiments of the disclosure are discussed with reference to wet allyl chloride becoming corrosive and dissolving iron. However, other olefins may become corrosive by reacting with water and/or other compounds in the organic stream and dissolve iron as well. As such, the present disclosure is not limited to wet allyl chloride.

For one or more embodiments, the process includes providing an ion exchange resin. For one or more embodiments, the ion exchange resin is a strong acid cation exchange resin. Strong acid cation exchange resins contain exchangeable cations, such as hydrogen ions ($H^+$). For one or more embodiments, the ion exchange resin includes active sites where ions can be exchanged. For one or more embodiments, the active sites of the ion exchange resin of the present disclosure can be represented by the following formula I:

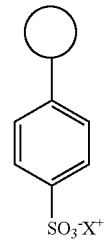

(Formula I)

wherein $X^+$ is a cation and the circle represents a solid support such as the resin.

For one or more embodiments, the process includes removing the iron ions from the organic stream by contacting the organic stream with the ion exchange resin. Removing the iron ions with the ion exchange resin can be accomplished as the iron ions contact the active site of the ion exchange resin. The ion exchange resin can exchange a cation from the active site with an iron ion in the organic stream. As discussed herein, the ion exchange resin is selected from strong acid cation exchange resins that have an exchangeable cation. In other words, the ion exchange resin can donate an ion and accept an ion. For the embodiments, the ion exchange resin can reduce iron ions present in the organic stream by exchanging cations with iron ions in the organic stream.

For one or more embodiments, the iron ions can be removed from the organic stream to provide the organic stream with an iron ion concentration of less than one weight percent, based on the total weight of the organic stream. In one embodiment, the iron ions are removed from the organic stream to provide the organic stream with an iron ion concentration of less than one part per million of the organic stream.

As discussed herein, the iron ions are removed from the organic stream by contacting the organic stream with the ion exchange resin. Contacting the organic stream with the ion exchange resin can be performed in either a batch or continuous mode. For example, the organic stream can be mixed with the ion exchange resin to form a heterogeneous solution. In an additional example, the organic stream can be passed through a fixed-bed reactor that contains the ion exchange resin. For the embodiments, mixing the organic stream with the ion exchange resin in a heterogeneous solution may be performed by known means for mixing, such as, but not limited to, stirring with an agitator or by inducing shear with a mixing element in a tubular reactor or loop reactor. Additionally, using combinations of the reactors and/or of batch and/or continuous modes to contact the organic stream with the ion exchange resin may also be used.

For the embodiments, the amount of the ion exchange resin needed to remove the iron ions from the organic stream will depend on an initial iron ion concentration of the organic stream. The initial iron ion concentration is the concentration of the iron ions prior to contacting the organic stream with the ion exchange resin. The initial iron ion concentration of the organic stream can vary between processes. For example, an amount of exposure, e.g., time, and the conditions of the exposure, e.g, the temperature of the organic stream, at which the organic stream is allowed to contact equipment containing iron can vary the initial iron ion concentration of the organic stream. Therefore, depending on the initial iron ion concentration of the organic stream the amount of the ion exchange resin will vary. However, enough of the ion exchange resin is used to provide the organic stream with an iron ion concentration that is less than one weight percent, based on the total weight of the organic stream. In one embodiment, enough of the ion exchange resin is used to provide the organic stream with an iron ion concentration of less than one part per million of the organic stream.

For one or more embodiments, the process includes contacting the organic stream having the iron ion concentration of less than one weight percent with a peroxide solution containing a stabilizer. As discussed herein, the organic stream can include an olefin and be used to form an oxirane by reacting the olefin with the peroxide in the peroxide solution. For one or more embodiments, the process of the present disclosure can reduce the amount of by-products formed during the reaction between the olefin and the peroxide in the peroxide solution. As discussed herein, stabilizers present in the peroxide solution, e.g., a hydrogen peroxide solution, can react with the iron ions and form a precipitate. For the embodiments, the organic stream can be used to produce epichlorohydrin by reacting the organic stream that includes allyl chloride and having the iron ion concentration of less than one weight percent with hydrogen peroxide in the peroxide solution that includes a stabilizer.

For one or more embodiments, the peroxide solution is a hydrogen peroxide solution containing a stabilizer, as discussed herein. However, as one skilled in the art would appreciate, other organic and/or inorganic hydroperoxides may be used for the production of the oxirane. Examples of other hydroperoxides that may be used include, but are not limited to, tert-butyl hydroperoxide, ethylbenzene hydroperoxide, acetyl peroxide, benzoyl peroxide, methyl ethyl ketone peroxide, cumene peroxide and combinations thereof.

Available sources of the hydrogen peroxide solution can be produced by the hydrolysis of a persulphuric acid and, more commonly, the successive hydrogenation and oxidation of a substituted alkylanthroquinone in a suitable solvent system. Both methods produce a hydrogen peroxide solution that can contain high levels of impurities such as solids and transition metal ions that are introduced during the production of the hydrogen peroxide solution. Hydrogen peroxide solutions with even trace levels of impurities tend to decompose during storage and/or use. Therefore, stabilizers are added to the hydrogen peroxide solution to reduce and/or prevent decomposition. Examples of stabilizers include, but are not limited to, organic phosphates, phosphoric acid, nitric acid, stannates, or mixtures thereof.

As discussed herein, the iron ions in the organic stream can react with stabilizers, e.g., organic phosphates, and form by-products such as iron phosphate precipitates. Removing the iron ions from the organic stream prior to contacting the organic stream with the hydrogen peroxide solution can help minimize the amount of by-products formed between the iron ions and stabilizers. By-products are solids which can foul the catalyst or restrict flow through the system. For the embodiments of the present disclosure reducing this by-product formation can also minimize production costs by reducing the need for measures to remove the by-product solids.

For one or more embodiments, the process includes maintaining the iron ion concentration of the organic stream to less than one weight percent, based on the total weight of the organic stream, preferably to less than one part per million of the organic stream before contacting the organic stream with the peroxide solution containing the stabilizer. For example, a distance and/or exposure of the organic stream between contacting the organic stream with the ion exchange resin and contacting the organic stream with the peroxide solution can be minimized. Additionally, the equipment used to transport or hold the organic stream having the iron ion concentration of less than one part per million to contact the peroxide solution can be of a non-ferrous materials (e.g., non-ferrous metal materials and/or non-metal materials), discussed more herein.

For one or more embodiments, the process further includes monitoring the iron ion concentration of the organic stream after removing the iron ions from the organic stream with the ion exchange resin. The amount of iron ions the ion exchange resin removes from the organic stream can decrease over time. As such, monitoring the iron ion concentration of the organic stream after contacting the ion exchange resin (e.g., downstream of the ion exchange resin) can help determine when the ion exchange resin is no longer removing the iron ions from the organic stream to at least below one weight percent, based on the total weight of the organic stream.

Monitoring the iron ion concentration can include positioning a monitoring device after contacting the organic stream with the ion exchange resin. Additionally, monitoring can include periodically taking samples of the organic stream to determine the iron ion concentration. Furthermore, monitoring can include visually determining when the precipitates begin to form between the iron ions and the stabilizers in the peroxide solution.

For one or more embodiments, the process further includes regenerating the ion exchange resin. Ion exchange resins can have a total capacity, which is a total number of chemical equivalents available for exchange per some unit weight or unit volume of the ion exchange resin. Depending on the application, it may be advantageous to regenerate the ion exchange resin at percentages of the total capacity. For example, the ion exchange resin can be regenerated when the ion exchange resin has reached 20 percent of the total capacity, 75 percent of the total capacity, or 100 percent of the total capacity. As discussed herein, the percent of the total capacity at which the ion exchange resin is regenerated can vary between applications. As such, the ion exchange resin can be regenerated within a range of from greater than zero percent of the total capacity to 100 percent of the total capacity.

For one or more embodiments, regenerating the ion exchange resin can include treating the ion exchange resin with an acid, e.g., an acid solution. Examples of acids include, but are not limited to, sulfuric acid, hydrochloric acid, and combinations thereof. The ion exchange resin can be treated with a regeneration solution including the acid. The acid solution can have an acid concentration within a range of 2 to 20 wt %, based on a total weight of the acid solution. The regeneration can be performed within a temperature range of 25 degrees Celsius (° C.) to 80° C.

For one or more embodiments, a volume of acid is used to generate a majority of the active sites of the ion exchange resin. The volume of acid can regenerate 70% or more of the active sites of the ion exchange resin and preferably 80% of more of the active sites of the ion exchange resin, based on a total number of active sites. As one skilled in the art can appreciate, the volume of acid used can depend on various factors and change between different processes. For example, one factor can include an amount of ion exchange resin being regenerated. For one or more embodiments, a flow rate of the acid solution is 2 bed volumes per hour. After regeneration the acid is rinsed off of the ion exchange resin with deionized water.

For one or more embodiments, the process further includes reacting the organic stream including an olefin and having the iron ion concentration of less than one weight percent with the peroxide solution to form the oxirane. As discussed herein, the reaction between the olefin and the peroxide solution is referred to as the epoxidation reaction. The epoxidation reaction can occur in the presence of a catalyst and one or more solvents. For the embodiments, the olefin can be the olefins as described herein. Additionally, the peroxide solution can be selected from the peroxide solutions as described herein. For one or more embodiments, the oxirane is epichlorohydrin.

Catalysts used in epoxidation reactions will eventually deactivate. The formation of by-products such as precipitates can increase the rate of deactivation by plugging the pores of the catalyst. As provided herein, the process for removing iron ions from the organic stream can help minimize the amount of by-products formed. Minimizing the by-products can reduce the rate at which the pores of the catalyst become plugged. Reducing the rate at which the pores of the catalyst become plugged can increase the lifetime of the catalyst as compared to a process using an organic stream where iron ions have not been removed. For the embodiments, increasing the lifetime of the catalyst and reducing the frequency at which the catalyst needs to be separated and regenerated can reduce the cost and time associated with epoxidation reactions.

The present disclosure further provides an oxirane product formed by the processes described herein. The oxirane product is formed by reacting the organic stream, including allyl chloride, with a peroxide solution. As discussed herein, the organic stream can contain iron ions that can react with stabilizers present in the peroxide solution. The iron ions can be removed from the organic stream with an ion exchange resin, as discussed herein, by contacting the organic stream with the ion exchange resin to provide the organic stream with an iron ion concentration of less than one weight percent based on the total weight of the organic stream. The organic stream having the iron ion concentration of less than one weight percent is contacted with a peroxide solution containing a stabilizer to form the oxirane. As discussed here, the peroxide solution can be a hydrogen peroxide solution and the oxirane can be epichlorohydrin.

Embodiments of the present disclosure further provide in FIG. 4 an exchange vessel 452 for use with the system and process of the present disclosure, where the exchange vessel 452 can be used to remove iron ions from the organic stream. In one or more embodiments, the exchange vessel 452 includes a first pipe 450 for transporting the organic stream 430 including allyl chloride and iron ions, where the organic stream 430 has the initial iron ion concentration. The first pipe 450 transports the organic stream 430 to the exchange vessel 452 that holds a solid support 454 with active sites that can remove iron ions from the organic stream 430 to provide the organic stream with an iron ion concentration of less than one weight percent based on the total weight of the organic stream. Organic stream 456 leaving the exchange vessel 452 has the iron ion concentration of less than 1 wt %, based on the total weight of the organic stream 430. For one or more embodiments, the solid support 454 with active sites is an ion exchange resin, and in particular, a strong acid cation exchange resin. As discussed herein, removing the iron ions with the ion exchange resin can be carried out in either a continuous, a semi-continuous, or in a batch process. The exchange vessel 452 can be selected from, but is not limited to, one or more continuous stirred tank reactors, tubular reactors, fixed-bed reactors, and combinations thereof. For one embodiment, the solid support 454 in the exchange vessel 452 is in a fixed bed. In an alternative embodiment, the solid support 454 in the exchange vessel 452 is in a slurry.

For one or more embodiments, the system 400 includes a second pipe 458 connected to an outlet 460 of the exchange vessel 452. The second pipe 458 can transport the organic stream 456 having the iron ion concentration of less than one weight percent, based on the total weight of the organic stream 430, from the exchange vessel 452 to the reaction vessel 406.

For one or more embodiments, the system 400 can include a third pipe 462 connected to the reaction vessel 406. The third pipe 462 can transport a peroxide solution 464 including a stabilizer. For one or more embodiments, the peroxide solution 464 is a hydrogen peroxide solution. The organic stream 456 including allyl chloride and having the iron ion concentration of less than one weight percent, based on the total weight of organic stream 456, can react with the peroxide solution 464 in the reaction vessel 406 to form the oxirane.

As seen in FIG. 4, the organic stream 456 and the peroxide solution 464 are introduced separately into the reaction vessel 406 via the second pipe 458 and the third pipe 462, respectively. In one or more embodiments, the organic stream 456 and the peroxide solution 464 can be combined prior to entering the reaction vessel 406.

For one or more embodiments, the outlet 460 and the second pipe 458 that transports the organic stream 456 from the exchange vessel 452 to the reaction vessel 406 can be of a non-ferrous metal material. Having the second pipe 458 constructed from non-ferrous metal materials can maintain the iron ion concentration of the organic stream 456 to less than one weight percent, based on the total weight of the organic stream 456, prior to contacting the organic stream 456 with the peroxide solution 464 to form the oxirane.

As discussed herein, the amount of iron ions the ion exchange resin removes from the organic stream can decrease over time. The iron ion concentration of the organic stream 456 can be monitored to determine when the iron ion concentration of the organic stream 456 is approaching or above one weight percent, based on the total weight of the organic stream 456. As such, the system can further include a monitoring device 466 positioned at the outlet 460 of the exchange vessel 452 or downstream from the exchange vessel 452 to measure the iron ion concentration in the organic stream 456 prior to contacting the organic stream 456 with the peroxide solution 464 in the reaction vessel 406.

The system can further include a fourth pipe 468 that can remove a reaction effluent 470 from the reaction vessel 406. The fourth pipe 468 can carry the reaction effluent 470 downstream for further processing that can include, but is not limited to, decantation, extraction, and/or distillation.

As discussed herein, the catalysts used in epoxidation reactions will eventually deactivate. Embodiments of the present disclosure are also directed to a process for regenerating such a deactivated catalyst, i.e., a catalyst that has been fouled during the reaction between the olefin and the peroxide compound to produce the oxirane. As discussed herein, the titanium silicalite catalysts (also referred herein to as "catalyst") can become fouled as the small pores of the titanium silicalite catalyst become plugged during the epoxidation reaction. When a titanium silicalite catalyst becomes fouled, the yield of the oxirane (e.g., epichlorohydrin, also referred to herein as "epi") during the epoxidation reaction can decrease. Thus, the phrase "fouled catalyst" refers to the performance of the catalyst. As mentioned above, a "fouled catalyst" is a catalyst that is contaminated with foulants, e.g, plugged with organic materials from the epoxidation reaction. As a result, access of the reactants to the catalyst is reduced and/or the catalytic activity of a fouled catalyst is reduced as compared to that of a corresponding fresh catalyst. For example, a fouled catalyst has decreased selectivity and/or decreased productivity and/or decreased yield as compared to a corresponding fresh catalyst. Thus, under the same operating conditions, the use of a fouled catalyst results in a decreased oxirane yield as compared that of a corresponding fresh catalyst, e.g., at least about a 25% decrease in epi productivity, and/or at least a 4% decrease in epi yield.

Once fouled, the titanium silicalite catalyst can be regenerated according to the methods of the present disclosure. Thus, a "regenerated catalyst" is a catalyst having a portion of its original catalytic activity renewed and/or restored.

As used herein, the phrase "epichlorohydrin productivity" refers to the amount of epi produced (i.e., the mass rate) divided by the catalyst amount (in volume). Epi productivity is expressed in lbs of Epi/hr/ft$^3$ of catalyst. As used herein, "oxirane yield" and/or "epichlorohydrin yield" is represented as a percentage and is determined by dividing the amount of oxirane produced during the epoxidation reaction by a theoretical maximum amount of oxirane produced at 100 percent (%) of the peroxide compound conversion to the oxirane.

As used herein, the phrase "epichlorohydrin selectivity" refers to the ratio of the molar amount of epi produced divided by the sum of the molar amount of epi produced and molar amount of byproduct produced, such as 1-chloro-2, 3-dihdroxypropane ("MCH") and 1-chloro-3-methoxy-2-hydroxypropane ("CMP"), and is expressed as a percentage.

Previous approaches have regenerated fouled catalysts by using thermal oxidation techniques. Thermal oxidation techniques can include a heat treatment by flowing gas through the fouled catalyst or static calcination. However, thermal oxidation techniques are not practical methods for in situ regeneration of a catalyst in a reactor due to the materials of construction that are used for the required temperatures of thermal oxidation, approximately 600 degrees Celsius (° C.). Additionally, other approaches have used chemical oxidation as an alternative to using thermal oxidation. However, these approaches use an oxidizing agent not present in the epoxidation reaction. Using an oxidizing agent not present in the epoxidation reaction can cause contamination and increase the cost of production by adding additional materials used during the epoxidation reaction.

As discussed herein, the process of the present disclosure provides a process for regenerating a titanium silicalite catalyst fouled during a reaction between the olefin and the peroxide compound to produce the oxirane. For one or more embodiments, the process includes contacting the fouled titanium silicalite catalyst with a regeneration solution including at least one oxidizing agent to provide a regenerated titanium silicalite catalyst. For one or more embodiments, the oxidizing agent can be selected from the group consisting of hydrogen peroxide, ozone, organic peroxide compounds, inorganic peroxide compounds, and combinations thereof. The oxidizing agent is preferably an oxidizing agent that is used in the epoxidation reaction where the titanium catalyst became fouled. In one embodiment, the oxidizing agent is hydrogen peroxide.

For one or more embodiments, the regeneration solution can have an oxidizing agent concentration of less than 0.50 weight percent (wt %) based on a total weight of the regeneration solution. For one or more embodiments, the regeneration solution can have an oxidizing agent concentration within a range of from 0.10 wt % to 0.49 wt %, preferably 0.2 wt % to 0.47 wt %, and more preferably 0.45 wt %.

For one or more embodiments, the process includes adjusting a pH of the regeneration solution to less than 2 prior to contacting the fouled titanium silicalite catalyst with the regeneration solution. In one embodiment, the pH of the regeneration solution is adjusted to 1 or less. For example, an acid can be added to the regeneration solution to adjust the pH of the regeneration solution to 1 or less. Examples of acids that can be used to adjust the pH include, but are not limited to, sulfuric acid, hydrochloric acid, phosphoric acid, acetic acid, and combinations thereof. In one embodiment, the pH of the regeneration solution is adjusted by adding sulfuric acid. Additionally, the pH of the regeneration solution can be adjusted by contact with ion exchange resins, supported acids and bases, organic acids, buffers, or combinations thereof.

For one or more embodiments, the regeneration solution can include an effluent from the epoxidation reaction between the olefin and the peroxide compound. The effluent arising from the epoxidation reaction may contain an amount of the oxidizing agent, which was not consumed during the epoxidation. For the embodiments, an oxidizing agent can be added to the effluent to provide the effluent with an oxidizing agent concentration of less than 0.50 wt % based on a total weight of the regeneration solution, exclusive of the titanium silicalite catalyst. The oxidizing agent added to the effluent can be selected from the oxidizing agents discussed herein. For one or more embodiments, the oxidizing agent added to the effluent can be the oxidizing agent used in the epoxidation reaction, e.g., hydrogen peroxide. For one or more embodiments, a pH of the effluent can be adjusted to less than 2 prior to contacting the fouled titanium silicalite catalyst with the regeneration solution. The pH of the effluent can be adjusted by the methods discussed herein.

For one or more embodiments, regenerating the titanium silicalite catalyst fouled during the epoxidation reaction can be performed in situ. As one skilled in the art can appreciate, the epoxidation reaction can occur in a batch process, semi-batch process, or continuous process. As such, there are a number of types of vessels and configurations of vessels, as discussed herein, to carry out the epoxidation reaction. For example, the titanium silicalite catalyst of the epoxidation reaction can be in a slurry with the olefin and peroxide compound to form the reaction mixture, as discussed herein. Additionally, the titanium silicalite catalyst can be in a fixed-bed configuration in the reaction mixture, as discussed herein.

So, for example, the system and process of the present disclosure can include regenerating the first part of the solid phase (e.g., the fouled titanium silicalite catalyst) suspended in the liquid aqueous phase from the separation vessel with the regeneration solution. In one embodiment, the first part of the solid phase can be contacted with the regeneration solution having an oxidizing agent concentration of less than 0.50 weight percent based on a total weight of the liquid regeneration solution, exclusive of the solid phase, to regenerate the solid phase. In an additional embodiment, the first part of the solid phase suspended in the liquid aqueous phase from the separation vessel can be regenerated by contacting the first part of the solid phase with a regeneration solution having a pH of less than 2.

For one or more embodiments, contacting the fouled titanium silicalite catalyst with the regeneration solution can include passing the regeneration solution through the reaction vessel, e.g., fixed-bed reaction vessel, in which the titanium silicalite catalyst is situated during the epoxidation reaction. Additionally, the titanium silicalite catalyst can be removed from the reaction vessel where the epoxidation reaction occurred and treated separately and returned to the reaction vessel once regenerated for a subsequent epoxidation reaction. The regeneration solution can be introduced continuously or non-continuously (by successive introductions of several doses of oxidizing agent) during the regeneration. Additionally, the regeneration solution can be added in one introduction. Contacting the fouled titanium silicalite catalyst can include mixing or stirring the regeneration solution with the fouled titanium catalyst. For one or more embodiments, regenerating the titanium silicalite catalyst is carried out within a temperature range of 0° C. to 100° C., preferably 25° C. to 90° C., and more preferably 40° C. to 80° C.

For one or more embodiments during the regeneration, the catalyst undergoing regeneration can be washed. Washing can include bringing the catalyst undergoing regeneration into contact with an organic compound. Examples of the organic compound include, but are not limited to, aliphatic, cyclic, aromatic, halogenated, supercritical, or alcoholic organic diluents. Water could be used alternatively. For one embodiment, the organic compound is methanol. For one or more embodiments, the catalyst undergoing regeneration is washed for a time period within a range of from 5 minutes to 60 minutes, preferably 30 minutes. Washing may be carried out, for example, by passing the washing solution through a fixed-bed of catalyst after regeneration, or by centrifuging solids from a slurry regeneration solution and transporting the solids to another vessel where washing may take place by agitating the solids in the washing solution.

Embodiments of the present disclosure further provide a process for regenerating the titanium silicalite catalyst fouled during the reaction between the olefin and the peroxide by contacting the fouled titanium silicalite catalyst with a regeneration solution having a pH of less than 2 and at least one oxidizing agent. For the embodiments, the regeneration solution can have an oxidizing agent concentration within a range of from 0.10 wt %-2.0 wt %, preferably 0.2 wt % to 1.0 wt %, and more preferably 0.3 wt % to 0.5 wt %. In one embodiment, the oxidizing agent concentration of the regeneration solution having a pH of less than 2 is 1 wt %, based on the total weight of the regeneration solution, exclusive of the titanium silicalite catalyst. For one or more embodiments, the oxidizing agent can be selected from the oxidizing agents discussed herein. Similarly, the pH of the regeneration solution can be adjusted as described herein.

Alternative embodiments of the present disclosure include a process for regenerating a titanium silicalite catalyst fouled during a reaction between an olefin and a peroxide compound to produce an oxirane, wherein the washing step is eliminated by contacting the titanium silicalite catalyst to be regenerated with a regeneration solution that comprises at least one oxidizing agent and further comprises an organic compound. Therefore, in certain embodiments of the disclosure, a fouled titanium silicalite catalyst is not subjected to a pre-regeneration wash and/or post-regeneration wash. It was surprisingly discovered that it is possible to regenerate a titanium silicalite catalyst by treating a silicalite catalyst with a regeneration solution comprising at least one oxidizing agent and further comprising an organic compound, thereby eliminating the step(s) of pre- and/or post-regeneration wash. For example, the regeneration solution can include an oxidizing agent concentration of 0.5 to 5 weight percent (wt %) based on a total weight of the regeneration solution, exclusive of the titanium silicalite catalyst; and an organic compound at 5 to 95 weight percent (wt %) based on a total weight of the regeneration solution, exclusive of the titanium silicalite catalyst.

For one or more embodiments, the regeneration solution can include additional materials. Examples include, but are not limited to iron ions and other metals.

For the embodiments of the present disclosure, the process applies to fouled catalysts of titanium silicalite type, and in particular to those used in a reaction between the olefin and the peroxide compound to form the oxirane, e.g., reacting allyl chloride with hydrogen peroxide to form epichlorohydrin. Catalysts used in epoxidation reactions can be selected from heterogeneous catalysts, as discussed herein.

The oxirane product prepared by the system and process of the present disclosure can be used in various applications. In particular, the oxirane, such as epichlorohydrin, produced by the system and process of the present disclosure can be used in the production of epoxy resins as described, for example, in Ullman's Encyclopedia of Industrial Chemistry, 5. ed., Vol. A9, pp. 547-562, incorporated herein by reference. Epoxy resins are high performance thermosetting resins which are used, for example, in coatings, electrical laminates, electronic encapsulants, adhesives, and composites.

As an illustration of the present disclosure, epichlorohydrin produced by the process of the system and present disclosure can also be used in the production of synthetic glycerine, elastomers, specialty water treatment chemicals, and wet strength resins for paper production and surfactants.

EXAMPLES

The following examples further illustrate the present disclosure in detail, but are not to be construed to limit the scope of the disclosure.

Epoxidation Reaction Examples

The following Examples 1-14 and Comparative Examples A-I illustrate various embodiments of the process for producing the oxirane by an epoxidation reaction.

Materials

Catalyst, titanium silicalite zeolite (TS-1), available from Süd-Chemie.
Catalyst, Methyltrioxorhenium, available from Süd-Chemie.
Olefin, allyl chloride (99.4% purity), obtained from The Dow Chemical Company.
Olefin, 1-Octene, available from Sigma Aldrich.
Olefin, Styrene, available from Sigma Aldrich.
Olefin, Allyl alcohol, available from Sigma Aldrich.
Peroxide compound, hydrogen peroxide solution (30 wt %/aq and 50 wt %/aq), available from VWR.
Alcohol, Methanol, available from Sigma Aldrich.
Co-catalyst Pyrazole, available from Sigma Aldrich.
Oxirane, epichlorohydrin, available from Sigma Aldrich.
Non-reactive co-solvent, 1,2-dichlorobenzene, available from Sigma Aldrich.
Non-reactive co-Solvent, dichloromethane, available from Sigma Aldrich.
Water
Test Methods
Gas Chromatography (GC)
Gas chromatography was performed on an HP 6890 series G1530A GC with an HP 7682 series injector and FID detection. An HP-1701 14% cyanopropyl phenyl methyl column of length 60.0 m, diameter 320.00 μm, and thickness 1.00 μm was used at temperatures from 35° C. to 250° C.
Peroxide Testing
Peroxide amounts were analyzed by iodometric titration using 0.01N sodium thiosulfate. The peroxide concentration may be calculated as follows: ppm $H_2O_2$=(mL titrant used) (0.01 N)(17000)/g sample. Titrations were performed using a Mettler Toledo DL5x V2.3 titrator with a DM140 sensor.
Reaction Vessel
The reactor used in the following Examples was a 750-mL jacketed glass reactor with a stainless steel cooling coil, thermocouple, mechanical stirrer, addition funnel, $N_2$ purge with gas scrubber, and reflux condenser/cold finger combination.

Example 1 and Example 2

In Examples 1 and 2,1,2-dichlorobenzene was used as a non-reactive co-solvent in an epoxidation reaction; and the catalyst from the Example 1 reaction was reused with the same equivalents and reaction conditions in Example 2.
Allyl chloride (247.39 g), TS-1 catalyst (6.946 g), methanol (24.25 g), and 1,2-dichlorobenzene (110.40 g) were added to a reactor. The contents of the reactor were brought to 25° C. After the contents of the reactor were brought to 25° C., a hydrogen peroxide solution (30 wt %/aq., 85.34 g) was added to the addition funnel to form the reaction mixture. The reaction mixture was stirred at 600 revolutions per minutes (rpm), and the exothermic reaction raised the temperature to 40° C., where it was maintained using the cooling coil.
Samples were taken from the reactor by removing an aliquot with a syringe while the stirring was stopped, such that only a portion of the organic phase was removed. The sample was filtered using a 0.45 micrometer (um) syringe filter to remove any catalyst particles, and was analyzed by gas chromatography (GC).
When the epoxidation reaction was deemed complete by epi analysis via GC (after 60 minutes), the reactor mixture were drained equally into two 250 mL centrifuge tubes, and centrifuged at 3000 rpm and 0° C. for 30 minutes. The liquid was decanted from the catalyst into a separatory funnel, where the liquid organic phase and the liquid aqueous phases were collected separately. Both phases were analyzed by GC and the amount of peroxide remaining was determined by titration with sodium thiosulfate. The results of these examples are reported in Table II.

Comparative Example A and Comparative Example B

In Comparative Example A an epoxidation reaction with low methanol levels and no non-reactive co-solvent was carried out; and the catalyst from the Comparative Example A reaction was reused with the same equivalents and reaction conditions in Comparative Example B.
Example 1 was repeated with the following changes, 353.77 g allyl chloride, 6.924 g TS-1 catalyst, 24.40 g methanol, 85.83 g of hydrogen peroxide solution, and no 1,2-dichlorobenzene was used. The reaction was deemed complete by epi analysis via GC after 120 minutes. The results of these comparative examples are reported in Table II.

Comparative Example C and Comparative Example D

In Comparative Example C, an epoxidation reaction was carried out with higher methanol and no non-reactive co-solvent; and the catalyst from the Comparative Example C reaction was reused with the same equivalents and reaction conditions in Comparative Example D.
The procedure in Example 1 was repeated with the following changes: 119.55 g allyl chloride, 6.881 g TS-1 catalyst, 239.07 g methanol, 8 g of hydrogen peroxide solution, and no 1,2-dichlorobenzene was used. The reaction was deemed complete by epi analysis via GC after 120 minutes. The results of these comparative examples are reported in Table II.

Comparative Example E and Comparative Example F

In Comparative Example E, an epoxidation reaction was carried out with no methanol and no non-reactive co-solvent, and the catalyst from the Comparative Example E reaction was reused with the same equivalents and reaction conditions in Comparative Example F except that the reaction time was extended for more conversion.
The procedure in Example 1 was repeated with the following changes: 382.0 g allyl chloride, 6.97 g TS-1 catalyst, 239.07 g methanol, 85.20 g of hydrogen peroxide solution, no 1,2-dichlorobenzene and no methanol was used.

The reaction was deemed complete by epi analysis via GC after 240 minutes. The results of these results are reported in Table II.

Example 3 and Example 4

In Example 3, 1,2-dichlorobenzene was used as a nonreactive co-solvent in an epoxidation reaction; and the catalyst from the reaction of Example 3 was reused in Example 4 with the same equivalents and reaction conditions as in Example 3.

The procedure in Example 1 was repeated with the following changes: 288.0 g of allyl chloride, 6.909 g of the TS-1 catalyst, 47.06 g of methanol, 43.67 g of 1,2-dichlorobenzene, and 85.20 g of the hydrogen peroxide solution. The results of these examples are reported in Table II.

Comparative Example G and Comparative Example H

In Comparative Example G, an epoxidation reaction was carried out with the same equivalents and reaction conditions given in Example 1 of Chinese Patent Application No. CN 200710039080.1; and the catalyst from the Comparative Example G reaction was reused with the same conditions in Comparative Example H except that the reaction time was extended for more conversion.

Allyl chloride (400.62 g) and TS-1 catalyst (10.05 g) were added to a reactor. The hydrogen peroxide solution (60.01 g) was added to the addition funnel, and then added to the reactor slowly after the allyl chloride/catalyst mixture was brought to about 25° C. The mixture was stirred at 1000 rpm, and the exothermic reaction raised the temperature up to 40° C., where it was maintained using the cooling coil.

After 60 minutes the reactor contents were drained equally into two 250 mL centrifuge tubes, and then centrifuged at 3000 rpm and 0° C. for 30 minutes. The liquid was decanted from the catalyst into a separatory funnel, where the organic and aqueous phases were collected separately. Both phases were analyzed by gas chromatography (GC) and the amount of peroxide remaining was determined by titration with sodium thiosulfate. The results of these examples are reported in Table II.

Example 5 and Comparative Example I

In Example 5 and Comparative Example I, reactions of epichlorohydrin and methanol were carried out to demonstrate the advantage of the presence of two liquid phases in the reactor. In Example 5 the reaction of epichlorohydrin and methanol was carried out in the presence of 1,2-dichlorobenzene and water, so that two liquid phases were present. In Comparative Example I, only 1,2-dichlorobenzene, and no water, was used so that only one liquid phase was present.

In Example 5, epichlorohydrin (249.0 g), 1,2-dichlorobenzene (110.0 g), methanol (23.70 g), and water (85.39 g) were added to the reactor and stirred at 40° C. and 600 rpm. After 120 minutes the reactor contents were drained equally into two 250 mL centrifuge tubes, and then centrifuged at 3000 rpm and 0° C. for 30 minutes. The liquid was decanted from the catalyst into a separatory funnel, where the organic and aqueous phases were collected separately. Both phases were analyzed by gas chromatography (GC). The results of this example are reported in Table I.

The same procedure was used in Comparative Example I, except that no water was added. The results of this example are reported in Table II.

Examples 6-13

The same procedure as described in Example 1 above was used in these examples except that the amount of the components were as described in Table I. The results are reported in Table II.

Example 14

The same procedure as described in Example 1 above was used in this example except that that the amounts of the components were as described in Table I. Allyl chloride (161.85 g), dichloromethane (109.7 g), pyrazole (2.05 g), and methyltrioxorhenium catalyst (0.3191 g) were added to a reactor. The hydrogen peroxide solution (59.98 g) was added to the addition funnel, and then added to the reactor slowly after the allyl chloride/catalyst/methanol mixture was cooled to about 9° C. The reaction was deemed complete by epi analysis via GC after 300 minutes. The organic layer was washed with two 250 mL portions of 0.1N sodium thiosulfate and then with two 250 mL portions of water. The organic layer was analyzed by GC and the amount of peroxide remaining in the aqueous layer was determined by titration with sodium thiosulfate. The results of this example are reported in Table II.

TABLE I

| | Components | | | | | |
|---|---|---|---|---|---|---|
| | Allyl Chloride (g) | TS-1 Catalyst (g) | Methanol (MeOH) (g) | 1,2-dichlorobenzene (g) | $H_2O_2$ Solution (g) | Reaction Complete (min) |
| Ex 1 | 247.39 | 6.946 | 24.25 | 110.40 | 85.34 | — |
| Ex 2 | 247.39 | 6.946 | 24.25 | 110.40 | 85.34 | — |
| Comp. A | 353.77 | 6.924 | 24.40 | — | 85.83 | 120 |
| Comp. B | 353.77 | 6.924 | 24.40 | — | 85.83 | 120 |
| Comp. C | 119.55 | 6.881 | 239.07 | — | 85.21 | 120 |
| Comp. D | 119.55 | 6.881 | 239.07 | — | 85.21 | 120 |
| Comp. E | 382.0 | 6.97 | — | — | 85.20 | 240 |
| Comp. F | 382.0 | 6.97 | — | — | 85.20 | 240 |
| Ex 3 | 288.00 | 6.909 | 47.06 | 43.67 | 85.20 | — |
| Ex 4 | 288.00 | 6.909 | 47.06 | 43.67 | 85.20 | — |
| Comp. G | 400.62 | 10.05 | — | — | 60.01 | — |
| Comp. H | 400.62 | 10.05 | — | — | 60.01 | — |
| Ex 5 | Epichlorohydrin 249.0 | — | 23.70 | 110.0 | Water 85.39 | — |
| Comp. I | Epichlorohydrin 249.0 | — | 23.70 | 110.0 | — | — |

TABLE I-continued

| | Components | | | | | |
|---|---|---|---|---|---|---|
| | Allyl Chloride (g) | TS-1 Catalyst (g) | Methanol (MeOH) (g) | 1,2-dichlorobenzene (g) | $H_2O_2$ Solution (g) | Reaction Complete (min) |
| Ex 6 | 244.95 | 10.507 | 24.09 | 112.77 | 85.81 | — |
| Ex 7 | 242.11 | 13.815 | 24.20 | 110.1 | 85.22 | — |
| Ex 8 | 290.80 | 6.94 | 23.76 | 110.85 | 42.87 | 180 |
| Ex 9 | 247.74 | 6.884 | 25.35 | 110.81 | 127.73 | 120 |
| Ex 10 | 248.21 | 6.906 | 23.71 | 112.40 | 51.12 (50 wt %/aq) | — |
| Ex 11 | 1-Octene(1) 247.97 | 6.931 | 24.53 | 110.15 | 85.38 | — |
| Ex 12 | Styrene(2) 250.95 | 6.9414 | 24.30 | 110.48 | 85.66 | 240 |
| Ex 13 | Allyl alcohol(3) 247.9 | 6.948 | 24.15 | 110.45 | 85.32 | 240 |
| Ex 14 | 161.85 | Methyltrioxorhenium 0.3191 | Pyrazole 2.05 | DCM 109.7 | 59.98 | 300 |

Notes for Table I:
(1) 1-octene was used instead of allyl chloride
(2) styrene was used instead of allyl chloride
(3) allyl alcohol was used instead of allyl chloride

TABLE II

| | Results | | | | | | |
|---|---|---|---|---|---|---|---|
| | Non-reactant Solvent | MeOH wt. % | Reaction Time (min) | Yield | $H_2O_2$ conversion | Selectivity | CMP/epi (wt.) | MCH/epi (wt.) |
| Ex 1 | 1,2-DCB | 5% | 60 | 94.0% | 99.3% | 94.7% | 0.012 | 0.004 |
| Ex 2 | 1,2-DCB | 5% | 120 | 93.1% | 99.2% | 93.8% | 0.016 | 0.005 |
| Comp. A | None | 5% | 120 | 90.9% | 99.5% | 91.4% | 0.012 | 0.002 |
| Comp. B | None | 5% | 180 | 86.6% | 99.2% | 87.3% | 0.019 | 0.007 |
| Comp. C | None | 53% | 120 | 93.7% | 99.7% | 94.0% | 0.029 | 0.005 |
| Comp. D | None | 53% | 180 | 91.8% | 97.8% | 93.9% | 0.032 | 0.005 |
| Comp. E | None | — | 240 | 85.0% | 92.4% | 92.1% | 0.000 | 0.120 |
| Comp. F | None | — | 300 | 44.8% | 84.0% | 53.3% | 0.000 | 0.226 |
| Ex 3 | 1,2-DCB | 10% | 60 | 90.2% | 99.7% | 90.4% | 0.002 | 0.001 |
| Ex 4 | 1,2-DCB | 10% | 120 | 90.3% | 99.6% | 90.7% | 0.015 | 0.003 |
| Comp. G | None | 0% | 60 | 77.2% | 94.5% | 81.7% | 0.000 | 0.105 |
| Comp. H | None | 0% | 240 | 75.6% | 96.2% | 78.6% | 0.000 | 0.097 |
| Ex 5 | 1,2-DCB | 5% | 120 | — | — | — | 0.005 | 0.002 |
| Comp. I | 1,2-DCB | 5% | 120 | — | — | — | 0.014 | 0.000 |
| Ex 6 | 1,2-DCB | 5% | 60 | 92.1% | 99.5% | 92.5% | 0.016 | 0.006 |
| Ex 7 | 1,2-DCB | 5% | 60 | 92.3% | 99.4% | 92.8% | 0.021 | 0.009 |
| Ex 8 | 1,2-DCB | 5% | 180 | 84.5% | 97.7% | 86.5% | 0.017 | 0.003 |
| Ex 9 | 1,2-DCB | 5% | 120 | 88.1% | 95.3% | 92.4% | 0.021 | 0.020 |
| Ex 10 | 1,2-DCB | 5% | 60 | 91.4% | 97.5% | 93.7% | 0.009 | 0.002 |
| Ex 11 | 1,2-DCB | 5% | 180 | 7.6% | 71.8% | 10.7% | — | — |
| Ex 12 | 1,2-DCB | 5% | 240 | 2.1% | 31.5% | 8.6% | — | — |
| Ex 13 | 1,2-DCB | 5% | 240 | 89.4% | 97.0% | 92.2% | — | — |
| Ex 14 | 1,2-DCB | — | 300 | 2.0% | 9.7% | 20.5% | — | — |

In Table II, "CMP" stands for 1-chloro, 3-methoxy, 2-propanol; "MCH" stands for 1-chloro-2,3-propanediol (monochlorohydrin); "epi" stands for epichlorohydrin; and "DCM" stands for dichloromethane.
In Table II, "Yield" is calculated as (the amount of epi produced)/(theoretical amount of epi if all $H_2O_2$ added was converted to epi); "$H_2O_2$ conversion" is calculated as (the total peroxide consumed during the reaction)/(peroxide added to the reaction); and "Selectivity" is calculated as (the amount of $H_2O_2$ converted to epi)/(the amount of $H_2O_2$ consumed during the reaction).

Table II is a summary of the results of the above experiments in the Examples and the Comparative Examples. The benefit of reducing the methanol (Comparative Example A and Comparative Example B) without adding a non-reactive co-solvent versus higher methanol without the non-reactive co-solvent (Comparative Example C and Comparative Example D) is demonstrated by lower amounts of CMP on the first use and reuse of the catalyst. The benefits of a non-reactive co-solvent (Examples 1 and 2) versus no non-reactive co-solvent (Comparative Example A. and Comparative Example B.) are demonstrated by shorter reaction time, higher yields, and higher selectivities on both the first use of the catalyst and on the reuse. The benefits of a non-reactive co-solvent (Examples 1 and 2) versus high methanol conditions similar to the literature (Comparative Example C and Comparative Example D) are demonstrated by higher yields, higher selectivities, and more particularly, much lower amounts of CMP on both the first use of the catalyst and the reuse. The benefits of using an alcohol/non-reactive co-solvent mixture (Examples 1 and 2) versus no solvent at all (Comparative Example G and Comparative Example H), as described in Chinese Patent Application No. CN 200710039080.1 is demonstrated by shorter reaction times, higher yields and selectivities, and in particular, much lower amounts of MCH. Comparative Example G and Comparative Example H demonstrate that the reaction conditions claimed in Chinese Patent Application No. CN 200710039080.1 does not lead to satisfactory reuse of the catalyst.

Example 5 and Comparative Example I demonstrate a further advantage of this invention, specifically the utility of the formation of multiple liquid phases in the inhibition of formation of the CMP byproduct. In Example 5 and Comparative Example I, the amounts of epichlorohydrin, methanol, and catalyst are equal. The only difference is the presence or absence of water, and therefore the existence of either one or two liquid phases. The existence of the system as two liquid phases significantly suppresses the formation of CMP.

Examples 6-10 demonstrate preferred embodiments of the present invention and are meant to show the utility of the invention over different reagent concentrations. Examples 11-13 demonstrate other embodiments of the present invention, showing the versatility of the invention in the epoxidation of several different olefins. Example 14 demonstrates the utility of the present invention with a homogeneous catalyst.

Separating Phases of a Mixture Examples

The following Examples 15-29e illustrate various embodiments of the process for separating phases of a mixture.

Materials

Catalyst, titanium silicalite zeolite (TS-1), available from Süd-Chemie.

Olefin, allyl chloride (99.4% purity), obtained from The Dow Chemical Company.

Peroxide compound, hydrogen peroxide solution (30 wt %/aq.), available from Sigma Aldrich.

Alcohol mixture, Methanol, available from Sigma Aldrich.

Oxirane, epichlorohydrin, available from Sigma Aldrich.

Non-reactive co-solvent, 1,2-dichlorobenzene, available from Sigma Aldrich.

Water

All materials were used as-is without further purification or modification.

Test Methods

Gas Chromatography (GC)

The analysis of organic components in samples was performed on a Hewlett Packard 6890 series G1530A gas chromatography with a Hewlett Packard 7682 series injector and flame ionization detector.

Example 15

Separating Phases of a Reaction Mixture

Example 15 illustrates an embodiment of the process of the present disclosure. Example 15 illustrates separating the liquid aqueous phase and the liquid organic phase, where the first portion of the solid phase catalyst remains in the liquid aqueous phase.

Example 15

A reaction mixture including the reaction products of an epoxidation reaction had the following composition: TS-1 catalyst (1 wt %), water (15.2 wt %), hydrogen peroxide (3.1 wt %), epichlorohydrin (8.6 wt %), allyl chloride (30.1 wt %), methanol (4.3 wt %), and 1,2-dichlorobenzene (37.7 wt %), where the wt % is based on a total weight of the reaction mixture including the reaction products. The reaction mixture was received in a 1-liter jacketed glass separatory funnel at a rate of 23 gram/minute (g/min).

The reaction mixture, in the separatory funnel, was cooled and maintained at a temperature of 35° C. using a glycol-water mixture circulating through the separatory funnel jacket. The reaction mixture is allowed to settle in the separatory funnel and separate into a liquid aqueous phase containing the TS-1 catalyst and a liquid organic phase containing the TS-1 catalyst.

The liquid organic phase is pumped from the separatory funnel at a rate of 17.8 gram/minute (g/min). The liquid aqueous phase has and a rate of overflow from the separatory funnel of 5.2 gram/minute (g/min).

The resulting composition of the liquid aqueous phase, as analyzed by gas chromatography, is shown in Table III. The resulting composition of the liquid organic phase as analyzed by gas chromatography is shown in Table IV. The wt % of the components in Table I and Table II is based on a total weight of the liquid organic phase, excluding the TS-1 catalyst. The wt % of the TS-1 catalyst is based on gravimetric analysis, dry weight basis.

TABLE III

| Liquid Aqueous Phase | Wt % |
| --- | --- |
| TS-1 Catalyst | 4.2 |
| Water | 67.6 |
| Hydrogen Peroxide | 13.6 |
| Epichlorohydrin | 1.5 |
| Allyl Chloride | 0.4 |
| Methanol | 16.9 |

TABLE IV

| Liquid Organic Phase | Wt % |
| --- | --- |
| TS-1 Catalyst | 0.0 |
| Water | 0.2 |
| Epichlorohydrin | 10.8 |
| Allyl Chloride | 39.2 |
| Methanol | 0.6 |
| 1,2-dichlorobenzene | 49.2 |

As seen in Table III, a first part (4.2 wt %) of the TS-1 catalyst remained suspended with the liquid aqueous phase. This represents 95% of the total catalyst fed to the separatory funnel.

As seen in Table IV, the removed liquid organic phase did not contain the TS-1 Catalyst. However, a second part (approximately 5 wt %, not shown in Table I or Table II) of the TS-1 catalyst fell out of the liquid aqueous phase and settled through the liquid organic phase to a density driven position. The second part of the TS-1 catalyst was removed separately from the separatory funnel via a drain valve.

Examples 16-29e

Extracting the Oxirane and Olefin from the Liquid Aqueous Phase

The liquid aqueous phase, whose composition is shown in Table V, is used as a representative liquid aqueous phase that would be generated during a process to make epichlorohydrin utilizing allyl chloride and hydrogen peroxide.

Examples 16-29e illustrate the extraction of the oxirane and the olefin from the liquid aqueous phase.

Example 16

Liquid aqueous phase, as described above, and whose composition is shown in Table V (9.0258 g) was added to a 20-mL sample vial. 1,2-Dichlorobenzene (1.0097 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 17

The procedure of Example 16 was repeated except with the following changes: use 7.0071 g of liquid aqueous phase and 3.0072 g of 1,2-Dichlorobenzene.

Example 18

The procedure of Example 16 was repeated except with the following changes: use 5.0257 g of liquid aqueous phase and 5.0179 g of 1,2-Dichlorobenzene.

Example 19

Liquid aqueous phase (18.02 g), as described above, and whose composition is shown in Table V was added to a 100-mL glass jar. Allyl chloride (2.00 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table III.

Example 20

The procedure of Example 19 was repeated except with the following changes: use 13.98 g of liquid aqueous phase and 6.02 g of allyl chloride.

Example 21

The procedure of Example 19 was repeated except with the following changes: use 10.07 g of liquid aqueous phase and 10.05 g of allyl chloride.

Example 22

Liquid aqueous phase, as described above, and whose composition is shown in Table V (9.0233 g) was added to a 20-mL sample vial. 1-Chloropropane (1.0083 g) was added to the sample vial along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 23

The procedure of Example 22 was repeated except with the following changes: use 7.0092 g of liquid aqueous phase and 3.0015 g of allyl chloride.

Example 24

The procedure of Example 24 was repeated except with the following changes: use 5.0046 g of liquid aqueous phase and 5.0158 g of allyl chloride.

Example 25

Liquid aqueous phase, as described above, and whose composition is shown in Table V (17.99 g) was added to a 50-mL glass jar. Allyl Chloride (2.00 g) was added to the sample vial along with a magnetic stir bar. The mixture was stirred magnetically at a speed sufficient to generate adequate mixing of the two liquid phases (determined visually) at approximately 35° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 26

The procedure of Example 25 was repeated except with the following changes: use 14.02 g of liquid aqueous phase and 6.06 g of allyl chloride.

Example 27

The procedure of Example 25 was repeated except with the following changes: use 10.04 g of liquid aqueous phase and 10.01 g of allyl chloride.

Example 28a

Liquid aqueous phase, as described above, and whose composition is shown in Table V (90.0 g) was added to an 8-oz. glass jar. 1,2-Dichlorobenzene (10.04 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 28b

The liquid aqueous phase resulting from Example 28a was added to an 8-oz. glass jar. 1,2-Dichlorobenzene (10.02 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 28c

The liquid aqueous phase resulting from Example 28b and was added to an 8-oz glass jar. 1,2-Dichlorobenzene (10.07 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 28d

The liquid aqueous phase resulting from Example 28c was added to an 8-oz. glass jar. 1,2-Dichlorobenzene (10.12 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 28e

The liquid aqueous phase resulting from Example 28d was added to an 8-oz. glass jar. 1,2-Dichlorobenzene (10.00 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 29a

Liquid aqueous phase, as described above, and whose composition is shown in Table V (90.0 g) was added to an 8-oz. glass jar. Allyl chloride (10.02 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 29b

The liquid aqueous phase resulting from Example 29a was added to an 8-oz glass jar. Allyl chloride (10.01 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid, phases formed and were allowed to equilibrate. The phases were withdrawn individually by syringe, weighed, and analyzed by gas chromatography. A summary of the GC data for pertinent components is shown in Table V.

Example 29c

The liquid aqueous phase resulting from Example 29b was added to an 8-oz. glass jar. Allyl chloride (10.06 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 29d

The liquid aqueous phase resulting from Example 29c was added to an 8-oz. glass jar. 1,2-Dichlorobenzene (10.00 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

Example 29e

The liquid aqueous phase resulting from Example 29d was added to an 8-oz. glass jar. 1,2-Dichlorobenzene (10.07 g) was added to the glass jar along with a magnetic stir bar. The mixture was stirred magnetically at a speed sufficient to generate adequate mixing of the two liquid phases (determined visually) at approximately 21° C. Stirring was stopped after 10 minutes and two liquid phases formed and were allowed to equilibrate. The phases were withdrawn individually by syringe, weighed, and analyzed by gas chromatography. A summary of the GC data for pertinent components is shown in Table V.

TABLE V

| Example | Solvent used | aq:solvent (mass ratio) | total wt % by GC | | | |
|---|---|---|---|---|---|---|
| | | | MeOH | AlC | epi | 1,2-DCB |
| | Initial aq | | 19.84 | 0.13 | 1.10 | 0.04 |
| 16 | 1,2-DCB | 9:1 | 15.60 | 0.00 | 0.38 | 0.04 |
| 17 | 1,2-DCB | 7:3 | 15.77 | 0.00 | 0.19 | 0.04 |
| 18 | 1,2-DCB | 5:5 | 15.91 | 0.00 | 0.10 | 0.04 |
| 19 | AlC | 9:1 | 15.34 | 0.66 | 0.34 | 0.00 |
| 20 | AlC | 7:3 | 15.67 | 0.64 | 0.14 | 0.00 |
| 21 | AlC | 5:5 | 15.84 | 0.65 | 0.07 | 0.00 |
| 22 | NPC | 9:1 | 15.62 | 0.00 | 0.37 | 0.00 |
| 23 | NPC | 7:3 | 15.87 | 0.00 | 0.15 | 0.00 |
| 24 | NPC | 5:5 | 15.98 | 0.00 | 0.07 | 0.00 |
| 25 | AlC | 9:1 | 15.29 | 0.62 | 0.38 | 0.00 |

TABLE V-continued

| Example | Solvent used | aq:solvent (mass ratio) | total wt % by GC |  |  |  |
|---|---|---|---|---|---|---|
|  |  |  | MeOH | AlC | epi | 1,2-DCB |
| 26 | AlC | 7:3 | 15.48 | 0.75 | 0.15 | 0.00 |
| 27 | AlC | 5:5 | 15.73 | 0.71 | 0.08 | 0.00 |
| 28a | 1,2-DCB | 9:1 | 15.70 | 0.01 | 0.46 | 0.04 |
| 28b | 1,2-DCB | 9:1 | 15.85 | 0.00 | 0.30 | 0.04 |
| 28c | 1,2-DCB | 9:1 | 15.93 | 0.01 | 0.19 | 0.04 |
| 28d | 1,2-DCB | 9:1 | 15.97 | 0.01 | 0.12 | 0.05 |
| 28e | 1,2-DCB | 9:1 | 15.98 | 0.00 | 0.08 | 0.08 |
| 29a | AlC | 9:1 | 15.50 | 0.52 | 0.32 | 0.00 |
| 29b | AlC | 9:1 | 15.62 | 0.57 | 0.15 | 0.00 |
| 29c | AlC | 9:1 | 15.90 | 0.35 | 0.07 | 0.00 |
| 29d | AlC | 9:1 | 15.82 | 0.48 | 0.03 | 0.00 |
| 29e | AlC | 9:1 | 15.85 | 0.48 | 0.01 | 0.00 |

"aq" = Liquid Aqueous Phase;
"MeOH" = methanol;
"AlC" = allyl chloride;
"epi" = epichlorohydrin;
"1,2-DCB" = 1,2-dichlorobenzene;
"NPC" = 1-chloropropane.

Removing Iron Ions from an Organic Stream Examples

The following Examples 30-37 illustrate removing iron ions from an organic stream.

Materials

Organic stream, allyl chloride (99.4% purity) including 3.5 weight percent (wt %) of iron ions. Allyl chloride available from The Dow Chemical Company.

Ion exchange resin, AMBERLITE™ IR120 H (CAS#9002-23-7), available from The Dow Chemical Company.

Ion exchange resin, DOWEX™ DR-2030 (CAS#69011-20-7), available from The Dow Chemical Company.

Test Methods

X-Ray Fluorescent (XRF) Test

Samples were transferred to an XRF sample cup and analyzed using UniQuant on the Philips PW-2400 wavelength dispersive x-ray fluorescence spectrometer. UniQuant analyzes for more than 60 elements including all common metals (aluminum, zinc, vanadium, nickel, iron, manganese, cobalt, molybdenum, copper, titanium, calcium, magnesium, chromium, sodium, and potassium). UniQuant also analyzes for non-metals such as P, S and Cl. The accepted detection limit for most elements in this method is 0.1 wt % and the accuracy for this method is generally better than ±30% and can be dependent on the assumed matrix.

Inductively Coupled Plasma Spectrometry (ICP) Test

Samples were weighed into quartz crucibles and approximately 2 milliliters of sulfuric acid was added. The samples were ashed in a muffle furnace at 550° C. until all of the organic components were removed. The ash was then dissolved in aqua regia (nitro-hydrochloric acid), the samples were made up to weight with deionized water and they were analyzed using an ICP spectrometer.

Example 30

AMBERLITE™ IR120 H (ion exchange resin) (2.10 grams (g)) was placed into a 20-milliliter vial. The organic stream (21.12 g) was added to the vial containing the ion exchange resin. The contents of the vial were agitated with a magnetic stirrer for 16 hours. After the 16 hours, the agitation was stopped and a sample of the organic stream was collected with a syringe. The collected sample was filtered using a 0.45 micron syringe filter. The sample was analyzed by XRF to determine the iron ion concentration in the organic stream. The results are illustrated in Table VI.

Example 31

The procedure in Example 30 was repeated, but with the following changes: use 3.94 g of the ion exchange resin and 20.01 g of the organic stream.

Example 32

The procedure in Example 30 was repeated, but with the following changes: use 6.23 g of the ion exchange resin and 20.42 g of the organic stream.

Example 33

The procedure in Example 30 was repeated, but with the following changes: use 1.12 g of the ion exchange resin and 19.98 g of the organic stream.

Example 34

DOWEX™ DR-2030 (ion exchange resin) (0.18 g) was placed into a 20-milliliter vial. The organic stream (20.37 g) was added to the vial containing the ion exchange resin. The contents of the vial were agitated with a magnetic stirrer for 16 hours. After the 16 hours, the agitation was stopped and a sample of the organic stream was collected with a syringe. The collected sample was filtered using a 0.45 micron syringe filter. The sample was analyzed by ICP to determine the iron ion concentration in the organic stream. The results are illustrated in Table VI.

Example 35

The procedure in Example 34 was repeated, but with the following changes: use 0.32 g of the ion exchange resin, and 20.54 g of the organic stream.

Example 36

The procedure in Example 34 was repeated, but with the following changes: use 0.38 g of the ion exchange resin, and 20.51 g of the organic stream.

Example 37

The procedure in Example 34 was repeated, but with the following changes: use 0.52 g of the ion exchange resin, and 21.02 g of the organic stream.

TABLE VI

| Example (Ex) | Ion Exchange Resin (g) | Allyl Chloride (g) | Fe |
|---|---|---|---|
| Ex 30 | 2.10 | 21.12 | ND |
| Ex 31 | 2.94 | 20.01 | ND |
| Ex 32 | 6.23 | 20.42 | ND |
| Ex 33 | 1.12 | 19.98 | ND |
| Ex 34 | 0.18 | 20.37 | <1 ppm |
| Ex 35 | 0.32 | 20.54 | <1 ppm |
| Ex 36 | 0.38 | 20.51 | <1 ppm |
| Ex 37 | 0.52 | 21.02 | <1 ppm |

Table VI is a summary of Examples 30 through 37. In the table, "ND" stands for "none detected" by XRF, which means the iron ion concentration is less than 0.1 weight percent of the organic stream. The organic stream prior to removing the iron ions had an initial iron ion concentration of 3.5 weight percent, based on the total weight of the organic stream. As seen in Table VI, each example reduces the iron ion concentration of the organic stream to below one weight percent. Additionally, Examples 34 through 37 reduce the iron ion concentration of the organic stream to below one part per million of the organic stream.

Catalyst Regeneration Examples

Materials
Catalyst, titanium silicalite (TS-1), available from Süd-Chemie.
Olefin, allyl chloride (99.4% purity), obtained from The Dow Chemical Company.
Peroxide Compound, hydrogen peroxide solution (30-50 wt %/aq.), available from VWR.
Oxidizing agent, hydrogen peroxide solution (30-50 wt %/aq), available from VWR.
Alcohol, Methanol, available from Fisher Scientific.
Non-reactive co-solvent, 1,2-dichlorobenzene, available from Sigma Aldrich.
Test Methods
pH Measurement
The pH was measured on a Beckman model 35 pH meter using an Orion 8272BN combination electrode with 2M potassium chloride filling solution, calibrated daily with pH=4 and pH=7 buffers.
Gas Chromatography (GC)
The amount of organic components remaining in samples was determined by analysis on a Hewlett Packard 6890 series G1530A gas chromatography with a Hewlett Packard 7682 series injector and flame ionization detector.
Hydrogen Peroxide Titration
Peroxide amounts were analyzed by iodometric titration using 0.01N sodium thiosulfate. The peroxide concentration may be calculated as follows: ppm $H_2O_2$=(milliliters titrant used) (0.01 N)(17000)/gram sample. Titrations were performed using a Mettler Toledo DL5x V2.3 titrator with a DM140 sensor.
Epichlorohydrin (Epi) Yield
The epichlorohydrin yield is determined by taking the amount of Epi produced during epoxidation reaction/theoretical maximum amount of Epi produced at 100% $H_2O_2$ conversion to Epi, and is represented as a percentage.
Epichlorohydrin (Epi) Productivity
The "epichlorohydrin productivity" refers to the amount of epi produced (i.e., the mass rate (per unit time)) divided by the catalyst amount (in volume). Epi productivity is expressed in lbs of Epi/hr/ft$^3$ of catalyst.
Epichlorohydrin (Epi) Selectivity
Epichlorohydrin selectivity refers to the ratio of the molar amount of epi produced divided by the sum of the molar amount of epi produced and molar amount of byproduct produced, such as 1-chloro-2,3-dihdroxypropane ("MCH") and 1-chloro-3-methoxy-2-hydroxypropane ("CMP"), and is expressed as a percentage.
Titanium Silicalite TS-1 Catalysts Used in Examples 38-40 and Comparative Example J
In Examples 38-40 and Comparative Example J, three different states of the TS-1 catalyst are utilized: (1) fresh, (2) fouled, and (3) regenerated catalyst. A fresh TS-1 catalyst is a dry catalyst from a vendor.

For the purposes of Examples 38-40 and Comparative Example J, a "fouled TS-1" catalyst is in particular a catalyst that has been used continuously in an epoxidation reaction for approximately 70 hours and then partially dried in a vacuum oven at 60° C. for 15 minutes and contains 30 wt % of other components, based on a total weight of the partially dried TS-1 catalyst. For the purposes of Examples 38-40 and Comparative Example J, a regenerated TS-1 catalyst is in particular a TS-1 catalyst that has been regenerated and then partially dried in a vacuum oven at 60° C. for 15 minutes and contains 30 wt % of other components, based on a total weight of the regenerated TS-1 catalyst. The amount of material remaining in the fouled and regenerated catalysts was determined by measuring the weight lost after further calcining said catalysts at 600° C. for approximately 2 or more hours.

Examples 38-40

(1) Epoxidation Using a Fresh TS-1 Catalyst

Allyl chloride (52.3 wt %), methanol (5.2 wt %), 1,2-dichlorobenzene (23.2 wt %), and fresh TS-1 catalyst (1.4 wt %) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide, 17.9 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a separatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table VII.

(2) Epoxidation Using a Fouled TS-1 Catalyst

Allyl chloride (52.0 wt %), methanol (5.2 wt %), 1,2-dichlorobenzene (23.0 wt %), and a fouled TS-1 catalyst (2.0 wt %, equivalent to 7.8 g fresh TS-1 catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide, 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a separatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table VII.

TABLE VII

| Catalyst Used in Epoxidation | Epi Yield |
|---|---|
| Fresh TS-1 | 89.7% |
| Fouled TS-1 | 86.3% |

Table VII illustrates the decrease in activity of the TS-1 catalyst. As seen in Table VII, a fresh TS-1 catalyst produces an epi yield of 89.7% whereas the fouled TS-1 catalyst produces an epi yield of 86.3%.

Regenerated TS-1 Catalysts of Examples 38-40

Examples 38-40 illustrate various embodiments for regenerating a TS-1 catalyst. Example 38 illustrates regenerating a fouled TS-1 catalyst by using a regeneration solution having an oxidizing agent concentration of 0.45 wt %, based on a total weight of the regeneration solution. Example 39 illustrates regenerating a fouled TS-1 catalyst by using a regeneration solution having an oxidizing agent concentration of 0.45 wt %, based on a total weight of the regeneration solution and a pH of 1. Example 40 illustrates regenerating a fouled TS-1 catalyst by using an effluent of an epoxidation reaction having an oxidizing agent concentration of 0.45 wt %, based on a total weight of the regeneration solution Example 38

Regenerated TS-1 Catalyst 1

A fouled TS-1 catalyst (10.2 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A regeneration solution (349.6 g) having an oxidizing agent concentration of 0.45 wt % (hydrogen peroxide in water) was added to the reactor to from a mixture. The mixture was stirred at 600 revolutions per minute (rpm) and maintained at approximately 80° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate. The regenerated TS-1 catalyst was stirred with methanol (350 g) at ambient temperature (23° C.). After 30 minutes the mixture was divided into two 250 mL centrifuge tubes, and then centrifuged at 10000 rpm at 0° C. for 10 minutes. The regenerated TS-1 catalyst was recovered by decantation and dried in a vacuum oven at 60° C. for 15 minutes.

Example 39

Regenerated TS-1 Catalyst 2

A fouled TS-1 catalyst (10.2 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A pH of a regeneration solution having an oxidizing agent concentration of 1 wt % (hydrogen peroxide in water) based on the total weight of the regeneration solution was adjusted to 1 by adding sulfuric acid ($H_2SO_4$) (2.8 g). The pH adjusted regeneration solution (347.0 g) had an oxidizing agent concentration of 0.98 wt % based of the total weight of the regeneration solution was added to the reactor to from a mixture. The mixture was stirred at 600 revolutions per minute (rpm), and the mixture was maintained at approximately 80° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate. The regenerated TS-1 catalyst was stirred with methanol (350 g) at ambient temperature. After 30 minutes the mixture was divided into two 250 mL centrifuge tubes, and then centrifuged at 10000 rpm at 0° C. for 10 minutes. The regenerated TS-1 catalyst was recovered by decantation and dried in a vacuum oven at 60° C. for 15 minutes.

Example 40

Regenerated TS-1 Catalyst 3

A fouled TS-1 catalyst (10.2 g, equivalent to 7.8 g fresh TS-1) that had been used continuously in an epoxidation reaction of allyl chloride to epichlorohydrin for approximately 70 hours was added to a 750-mL jacketed glass reactor with a stainless steel cooling coil, thermocouple, mechanical stirrer, addition funnel, $N_2$ purge with gas scrubber, and reflux condenser/cold finger combination. An oxidizing agent 30 wt % $H_2O_2$ (1.17 g) was added to an aqueous effluent (79.02 g; composition:=21.4 wt % methanol, 0.012 wt % allyl chloride, 0.018 wt % allyl alcohol, 0.26 wt % epichlorohydrin, 0.16 wt % 1-chloro-3-methoxy-2-hydroxy propane, 0.052 wt % 1,2-dichlorobenzene, 0.39 wt % 1-chloro-2,3-dihydroxy propane, and 77.7 wt % water) to form a regeneration solution having an oxidizing concentration of 0.45 wt %, based on a total weight of the regeneration solution. The regeneration solution (80.19 g) was added to the reactor to form a mixture. The mixture was stirred at 600 rpm, and the mixture was maintained at approximately 80° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and analyzed by GC. The amount of peroxide remaining in the regeneration solution was determined by iodometric titration with sodium thiosulfate. The regenerated TS-1 catalyst was stirred with methanol (350 g) at ambient temperature. After 30 minutes the mixture was divided into two 250 mL centrifuge tubes, and then centrifuged at 10000 rpm at 0° C. for 10 minutes. The regenerated TS-1 catalyst was recovered by decantation and dried in a vacuum oven at 60° C. for 15 minutes.

Epoxidation Reactions Using Regenerated TS-1 Catalysts from Examples 38-40

To illustrate the utility of the process of the present disclosure the regenerated catalysts from Examples 38-40 were used in an epoxidation to form ephichlorohydrin (Epi). The epichlorohydrin yield, i.e., amount of Epi produced during epoxidation reaction/theoretical maximum amount of Epi produced at 100% $H_2O_2$ conversion to Epi, was determined for each example.

Epoxidation Reaction Using the Regenerated TS-1 Catalyst from Example 38

Allyl chloride (52.0 wt %), methanol (5.2 wt %), 1,2-dichlorobenzene (23.0 wt %), and the regenerated TS-1 catalyst from Example 38 (2.00 wt %, equivalent to 1.55 wt % fresh catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide, 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a separatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table VIII.

Epoxidation Reaction Using the Regenerated TS-1 Catalyst from Example 39

Allyl chloride (52.0 wt %), methanol (5.2 wt %), 1,2-dichlorobenzene (23.0 wt %), and the regenerated TS-1 catalyst from Example 39 (2.00 wt %, equivalent to 1.55 wt % fresh catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide, 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a separatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table VIII.

Epoxidation Reaction Using the Regenerated TS-1 Catalyst from Example 40

Allyl chloride (51.9 wt %), methanol (5.2 wt %), 1,2-dichlorobenzene (23.0 wt %), and regenerated catalyst from Example 39 (2.03 wt %, equivalent to 1.56 wt % fresh catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide; 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a separatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table VIII.

TABLE VIII

| Example | Epi Yield |
| --- | --- |
| Example 38 | 89.8% |
| Example 39 | 88.9% |
| Example 40 | 87.5% |

Comparing the results of Table VII with Table VIII it can be seen that the regenerated TS-1 catalyst of Example 38 gave approximately the same Epi yield as the fresh TS-1 catalyst. Similarly, the regenerated TS-1 catalyst from Example 39 gave slightly lower Epi yield results than the fresh TS-1 catalyst. Finally, the regenerated TS-1 catalyst from Example 40 gave approximately a 2% lower Epi yield than the fresh TS-1 catalyst.

However, the Epi yield of Examples 38-40 was within 2% and 1% higher than the fouled TS-1 catalyst. As one skilled in the art will appreciate, saving 1% of epichlorohydrin can save a significant amount of money when applied to a full-scale manufacturing plant.

Comparative Example J

A fouled TS-1 catalyst (10.12 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A pH of a regeneration solution having an oxidizing agent concentration of 1 wt % (hydrogen peroxide in water), based on the total weight of the regeneration solution, was adjusted to 6.9 by adding sodium hydroxide (NaOH). The pH adjusted regeneration solution (351.36 g) was added to the reactor to form a mixture. The mixture was stirred at 600 revolutions per minute (rpm), and the mixture was maintained at approximately 80° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate. The regenerated TS-1 catalyst was stirred with methanol (350 g) at ambient temperature. After 30 minutes the mixture was divided into two 250 mL centrifuge tubes, and then centrifuged at 10000 rpm at 0° C. for 10 minutes. The regenerated TS-1 catalyst was recovered by decantation and dried in a vacuum oven at 60° C. for 15 minutes.

Epoxidation Reaction Using the Regenerated Catalyst from Comparative Example J

Allyl chloride (52.1 wt %), methanol (5.2 wt %), 1,2-dichlorobenzene (23.2 wt %), and the regenerated catalyst from Comparative Example J (1.7 wt %, equivalent to 1.36 wt % fresh catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide; 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the TS-1 catalyst into a separatory funnel and allowed to separate into a liquid organic phase and a liquid aqueous phase. The liquid organic phase and the liquid aqueous phase were analyzed by GC. The amount of peroxide remaining in each phase was determined by iodometric titration with sodium thiosulfate. The Epi Yield was calculated and is shown Table IX.

TABLE IX

| Comparative Example | Epi Yield |
|---|---|
| Comparative Example J | 83.8% |

Comparing the results of Table VII with Table IX it can be seen that the regenerated TS-1 catalyst of Comparative Example J gave a significantly lower Epi yield than the fresh TS-1 catalyst. For example, the Comparative Example J Epi yield was approximately 5% lower than the fresh TS-1 catalyst. Additionally, comparing the Epi yield of the Comparative Example J with Examples 38-40, the Epi yield of the Comparative Example J is lower than each Example 38 through 40.

Additionally, the Epi Yield of Comparative Example J is lower than the fouled TS-1 catalyst in Table VII. It is known by those skilled in the art that residual NaOH left in the TS-1 catalyst pores can reduce the yield of epichlorohydrin. It is believed that the sodium ions ($Na^+$) can stabilize an active site of the TS-1 catalyst making it less reactive with the olefin such as allyl chloride. Additionally, the hydroxide ions ($OH^-$) can react with the epichlorohydrin produced and form 1-chloro-2,3-dihydroxy propane, which also reduces the yield of epichlorohydrin.

Comparative Example K and Examples 41-42

In Comparative Example K and Examples 41-42, three different states of the TS-1 catalyst are utilized: (1) fresh, (2) fouled, and (3) regenerated catalyst. For the purposes of Comparative Example K and Examples 41-42, a fresh TS-1 catalyst is a commercially available dry TS-1 catalyst, e.g., TS-1 beads of 1.6 to 2.5 mm particle size. Inert glass beads filled the space above and below the catalyst in the reactor. For the purposes of Comparative Example K and Examples 41-42, a fouled TS-1 catalyst is a TS-1 catalyst that has been used for continuously in an epoxidation reaction for approximately 20 hours and/or the Epi productivity has decreased by more than 25% of its maximum value. The "maximum value" for a TS-1 catalyst can be determined experimentally by methods known to the art, for example, by use of an epi productivity plot of a fresh or regenerated catalyst, e.g., the maximum value is the point at which the slope of the epi productivity curve changes from positive to negative. For the purposes of Comparative Example K and Examples 41-42, a regenerated TS-1 catalyst is a TS-1 catalyst that has been regenerated with a particular regeneration solution of interest and at an operating temperature of approximately 80° C. for more than 5 hours.

Comparative K $H_2O_2$ and Water Regeneration

Epoxidation Reaction. 150.1 g of fresh TS-1 catalyst (TS-1 beads; 1.6-2.5 mm), were placed in a 1.05" ID×49.125" long open tube reactor equipped with a recirculation loop (total volume of loop ~46 mL). The reactor was fed continuously (about 20 hours) with an aqueous (43 wt % $H_2O_2$ solution) feed rate of 1.0 mL/min and organic (6.35 wt % MeOH, 50.3 wt % Allyl Chloride, 42.9 wt % o-DCB mixture) feed rate of 5.0 mL/min with a recycle rate of 2.0 L/min. The reactor operated at 40° C.

The reactor contents (liquid contents, catalyst remained) were then emptied and blown down with nitrogen to remove the bulk of the reaction mixture prior to introduction of the regeneration solution. The operating temperature was 80° C. The regeneration process was done batch-wise and did not utilize methanol in the solution. No washing step was performed. After the regeneration process, the reactants were fed back at the same conditions mentioned above. For each regeneration solution batch, it was allowed that the initial $H_2O_2$ concentration was depleted to about 0.1 wt % before introducing a new batch with higher a $H_2O_2$ concentration.

Table X shows the epi productivity, epi selectivity and $H_2O_2$ concentration in the effluent at three different time periods using the fresh TS-1 catalyst. In particular, after one hour of operation the first sample was analyzed. After 5 hours of operation, when the Epi productivity reached a maximum amount, the second sample was analyzed. After 20 hours of operation, when a steady state was reached, the third sample was analyzed.

TABLE X

| Fresh TS-1 Catalyst | | | |
|---|---|---|---|
| Hours of operation | Epi Production lbs/hr/ft³ cat | Epi selectivity % | $H_2O_2$ concentration in effluent Wt % |
| 1 | 1.5 | 95.2 | 0.4 |
| 5 | 16.9 | 90 | 7.4 |
| 20 | 6.9 | 88.2 | 25.4 |

Table XI shows the starting $H_2O_2$ concentration for each of the five different regeneration solutions used during the regeneration process of Comparative Example K, i.e., the concentration of $H_2O_2$ in the regeneration solution prior to contacting the fouled TS-1 catalyst with the regeneration solution.

TABLE XI

| Batch Number | Starting $H_2O_2$ concentration of Comparative Regeneration solution Wt % |
|---|---|
| 1 | 1.07 |
| 2 | 1.04 |
| 3 | 1.29 |
| 4 | 1.56 |
| 5 | 1.54 |

Table XII shows the epi productivity, epi selectivity and $H_2O_2$ concentration in the effluent at three different time periods using the catalyst regenerated with the $H_2O_2/H_2O$ solutions under the similar epoxidation conditions as the TS-1 fresh catalyst. The first sample was analyzed after one hour of operation; the second sample was analyzed after 5 hours of operation when the Epi productivity reached a maximum amount; and the third sample was analyzed after 20 hours of operation when a steady state was reached.

TABLE XII

TS-1 Catalyst regenerated with the $H_2O_2/H_2O$ solutions

| Hours of operation | Epi Productivity lbs/hr/ft³ cat | Epi selectivity % | $H_2O_2$ concentration in effluent Wt % |
|---|---|---|---|
| 1 | 3.2 | 91.7 | 0.7 |
| 5 | 9.9 | 83.6 | 15.5 |
| 20 | 7.3 | 79.6 | 25.1 |

In comparing Tables X and XII, it can be seen that the epi productivity and $H_2O_2$ concentration in the effluent for the epoxidation reaction with fresh catalyst (Table IV) and the epoxidation reaction with $H_2O_2$/water solution (Table VI) remained about the same, see for example at the 20$^{th}$ hour of operation. However, the epi selectivity had a dramatic change. Regenerating with a solution of water and $H_2O_2$ yielded lower selectivity, and the productivity did not reach the same maximum as that of the fresh catalyst for the fifth hour of operation.

Example 41

$H_2O_2$/Water/Methanol Regeneration

The reactor contents (liquid contents, catalyst remained) were emptied (from the previous run, i.e., Comparative Example K) and blown down with nitrogen to remove the bulk of the reaction mixture prior to introduction of the regeneration solution. The operating temperature was 80° C. The regeneration process was done batch-wise with a total of 4 batches (each containing methanol). Each contained on average 1.4 wt % $H_2O_2$ and 15 wt % methanol as the starting composition. No washing step was performed. After the regeneration process, the reactants were fed back at the same conditions as in Comparative Example K. For each regeneration solution batch, the initial $H_2O_2$ concentration was depleted to about 0.1 wt % before introducing a new batch with a higher $H_2O_2$ concentration.

Table XIII shows the epi productivity, epi selectivity and $H_2O_2$ concentration in the effluent at three different time periods using the regenerated TS-1 catalyst, i.e., the catalyst regenerated with the $H_2O_2$, water and methanol solution. In particular, after one hour of operation the first sample was analyzed. After 5 hours of operation, when the Epi productivity reached a maximum amount, the second sample was analyzed. After 11 hours of operation, the last sample was taken for this run.

TABLE XIII

| Hours of operation | Description | Epi productivity Lbs/hr/ft³ cat | Epi selectivity % | H2O2 concentration in effluent |
|---|---|---|---|---|
| 1 | 1$^{st}$ sample | 1.24 | 21.5 | 0.5 |
| 5 | Epi peak | 11.5 | 84.3 | 10.1 |
| 11 | Last sample | 8.9 | 82.4 | 16.5 |

In comparing the results from the epoxidation reaction with fresh TS-1 catalyst and the regenerated TS-1 catalyst with $H_2O_2$/water solution (Tables X and XII, respectively), and regenerated TS-1 catalyst with $H_2O_2$/water/methanol solution (Table XIII), the methanol containing regeneration solution showed an improvement over the $H_2O_2$/water solution in Epi selectivity and Epi productivity (see, for example, the data for the 5$^{th}$ hour of operation).

Figure 5:
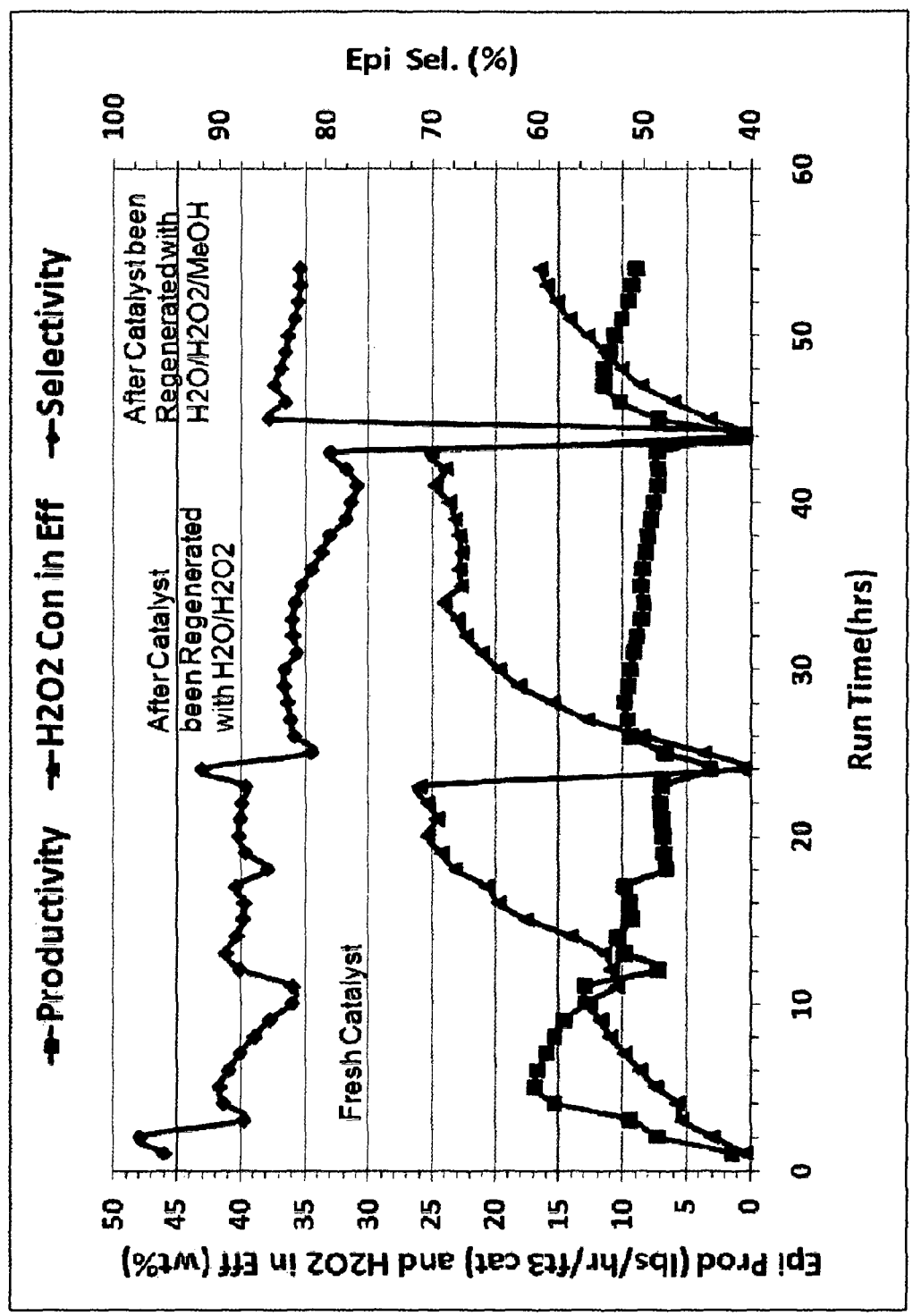
FIG. 5 is a graph depicting epi productivity, epi selectivity and $H_2O_2$ concentration data generated by a process according to certain embodiments of the present disclosure.

Turning now to FIG. 5, the epi productivity, epi selectivity and $H_2O_2$ concentration in the effluent using the fresh catalyst, using the catalyst regenerated with the solution of water and $H_2O_2$, i.e., without methanol; and using the same catalyst regenerated with the regeneration solution of water, $H_2O_2$ and methanol are graphically depicted. FIG. 5 shows plotted data generated from Comparative Example K and Example 41, represented as follows: epi productivity by squares; $H_2O_2$ concentration in effluent by triangles; and epi selectivity by diamonds.

Example 42

$H_2O_2$, Water and Methanol Regeneration

Epoxidation Reaction. 150.0 g of fresh TS-1 catalyst (TS-1 beads; 1.6-2.5 mm) were placed in a 1.05" ID×49.125" long open tube reactor equipped with a recirculation loop (total volume of loop 46 mL). The reactor was fed continuously (about 20 hours) with an aqueous (35 wt % $H_2O_2$ solution) feed rate of 1.0 mL/min and organic (6.2 wt % MeOH, 50.6 wt % Allyl Chloride, 42.8 wt % o-DCB mixture) feed rate of 5.0 mL/min with a recycle rate of 2.0 L/min. Reactor operated at 40° C.

The reactor contents (liquid contents, catalyst remained) were then emptied and blown down with nitrogen to remove the bulk of the reaction mixture prior to introduction of the regeneration solution. The fouled TS-1 catalyst was regenerated in situ with a regeneration solution of water, $H_2O_2$ and methanol. The operating temperature was 80° C. The regeneration process was done batch-wise with the regeneration solution having a methanol concentration of between 11 and 15 wt %. The initial concentration of $H_2O_2$ in the regeneration solution, i.e., the concentration of $H_2O_2$ in the regeneration solution prior to contact with the fouled TS-1 catalyst, was 1.401 wt %. When the $H_2O_2$ regeneration solution depleted to about 0.1 wt %, a pre-calculated amount of 35 wt % $H_2O_2$ solution was injected into the depleted regeneration solution to bring the concentration back to about 1 wt %; see Table XIV for initial batch concentrations and following concentrations of solution after each injection. After the regeneration process, the reactants were fed back at the same conditions as the initial epoxidation reaction in this Example.

TABLE XIV

| Batch | $H_2O_2$ concentration Wt % | Methanol concentration Wt % |
|---|---|---|
| 1 | 1.4 | 14 |
| 2 | 1.0 | 12.9 |
| 3 | 0.8 | 11.4 |
| 4 | 0.3 | 11.3 |
| 5 | 0.15 | 11.6 |

Table XV shows the epi productivity, epi selectivity and $H_2O_2$ concentration in the effluent at three different time periods using a fresh TS-1 catalyst, in particular, after one hour of operation the first sample was analyzed. After 4 hours of operation, when the Epi productivity reached a maximum amount, the second sample was analyzed. After 12 hours of operation, the third sample, an intermediate datum, was analyzed. After 17 hours of operation, when a steady state was reached, the fourth sample was analyzed.

TABLE XV

Fresh TS-1 Catalyst

| Hours of operation | Epi Production lbs/hr/ft$^3$ cat | Epi selectivity % | $H_2O_2$ concentration in effluent Wt % |
|---|---|---|---|
| 1 | 9.0 | 85.7 | 0.6 |
| 4 | 12.7 | 70.7 | 3.9 |
| 12 | 11.5 | 83.4 | 8.8 |
| 20 | 9.2 | 82.9 | 11.8 |

Table XVI shows the epi productivity, epi selectivity and $H_2O_2$ concentration in the effluent at three different time periods using the regenerated catalyst: in particular, after one hour of operation the first sample was analyzed. After 4 hours of operation, when the Epi productivity reached a maximum amount, the second sample was analyzed. After 12 hours of operation, when a steady state was reached, the third sample was analyzed.

TABLE XVI

Regenerated TS-1 Catalyst

| Hours of operation | Epi Production lbs/hr/ft$^3$ cat | Epi selectivity % | $H_2O_2$ concentration in effluent Wt % |
|---|---|---|---|
| 1 | 3.5 | 86.3 | 0.4 |
| 4 | 12.9 | 86.5 | 3.9 |
| 12 | 10 | 85.5 | 12.0 |

In comparing Tables XV and XVI, one can see that regenerating a titanium silicate catalyst with a solution containing $H_2O_2$/water/MeOH improved the selectivity by 2.1%, comparing the 12$^{th}$ hour of operation.

Figure 6:
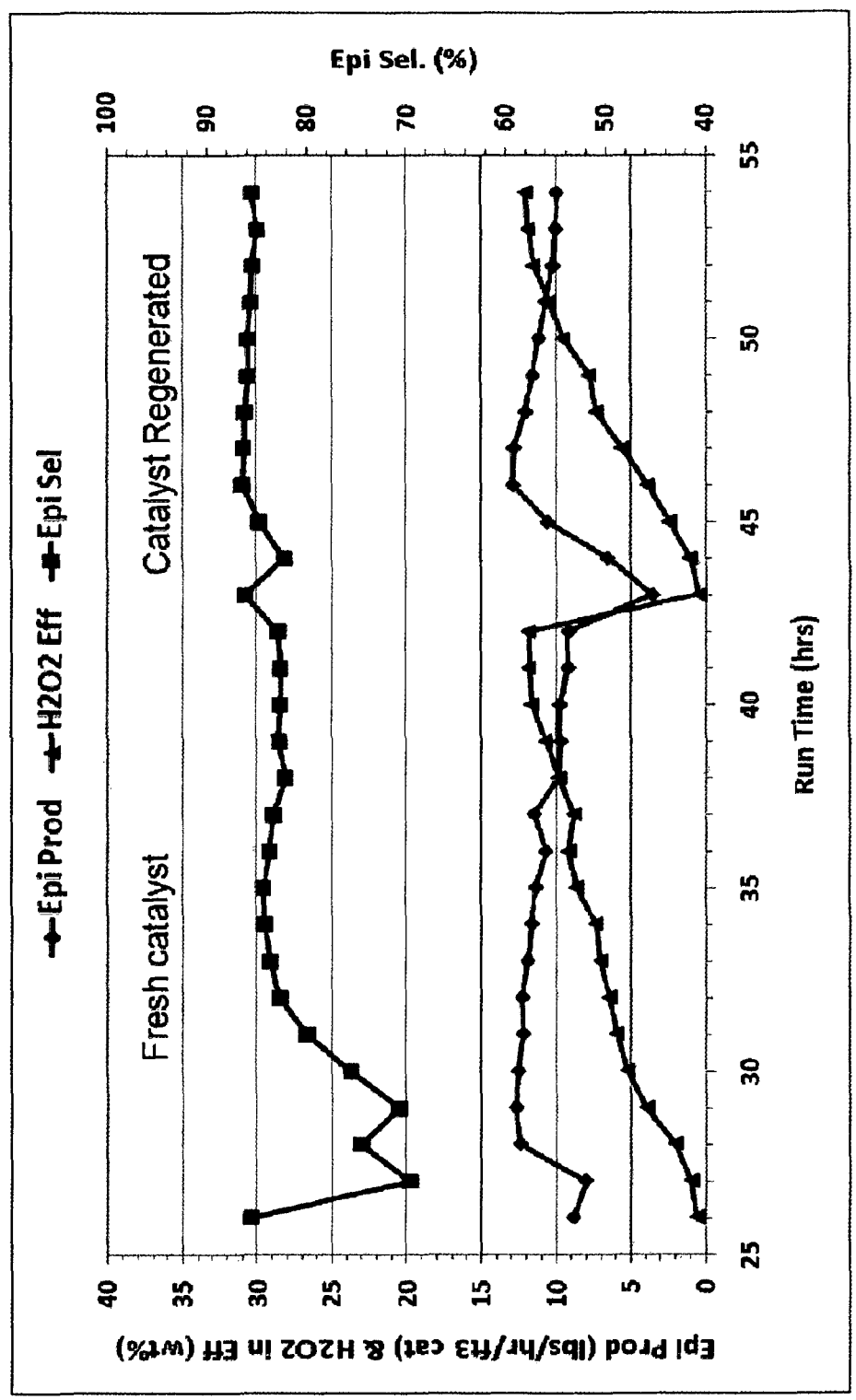
FIG. 6 is a graph depicting epi productivity, epi selectivity and $H_2O_2$ concentration data generated by a process according to certain embodiments of the present disclosure.

Turning now to FIG. 6, the epi productivity, epi selectivity and $H_2O_2$ concentration in the effluent using the fresh catalyst and the catalyst regenerated with the regeneration solution of water, $H_2O_2$ and methanol are graphically depicted. FIG. 6 shows plotted data generated from Example 42, represented as follows: epi productivity by diamonds; $H_2O_2$ concentration in effluent by triangles; and epi selectivity by squares. It can be seen that selectivity improved and that the productivity and $H_2O_2$ concentration follow similar patterns as before.

Examples 43-46 and Comparative Example L

The fresh catalyst used for Examples 43-46 and Comparative Example L was the same type of fresh TS-1 catalyst used in Examples 38-40, above (see Table VII for epi yield data). For the purposes of Examples 43-46 and Comparative Example L, a fouled TS-1 catalyst is in particular a catalyst that delivers an epi yield less than that of a fresh catalyst under same or similar conditions, e.g., 96% of the yield delivered by a fresh catalyst. For the purposes of Examples 43-46, a regenerated TS-1 catalyst is a TS-1 catalyst that has been regenerated and then partially dried in a vacuum oven at 60° C. for 15 minutes and contains 30 wt % of other components, based on a total weight of the regenerated TS-1 catalyst. Results of Examples 43-46 and Comparative Example L are provided in Table XVII.

Example 43

A fouled TS-1 catalyst (10.1 g, equivalent to 7.8 g fresh TS-1) was added to a 750 mL jacketed glass reactor with a stainless steel cooling coil, thermocouple, mechanical stirrer, addition funnel, $N_2$ purge with gas scrubber, and reflux condenser/cold finger combination. A regeneration solution (350.3 g) having an oxidizing agent concentration of 2.0 wt % hydrogen peroxide, 35.0% methanol and 63% de-ionized water was added to the reactor to form a mixture. The mixture was stirred at 600 revolutions per minute (rpm) and maintained at approximately 40° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate to be 1.96%. The regenerated TS-1 catalyst was recovered by decantation and dried in a vacuum oven at 60° C. for 15 minutes.

Example 44

A fouled TS-1 catalyst (10.0 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A regeneration solution (352.2 g) having an oxidizing agent concentration of 0.5 wt % hydrogen peroxide, 20.0% methanol and 79.5% de-ionized water was added to the reactor to form a mixture. The mixture was stirred at 600 revolutions per minute (rpm) and maintained at approximately 40° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate to be 0.17%. The regenerated TS-1 catalyst was recovered by decantation and dried in a vacuum oven at 60° C. for 15 minutes.

Example 45

A fouled TS-1 catalyst (10.1 g, equivalent to 7.8 g fresh TS-1) was added to a 750-mL jacketed glass reactor with a stainless steel cooling coil, thermocouple, mechanical stirrer, addition funnel, N$_2$ purge with gas scrubber, and reflux condenser/cold finger combination. A regeneration solution (349.7 g) having an oxidizing agent concentration of 5.0 wt % hydrogen peroxide, 5.0% methanol and 90.0% de-ionized water was added to the reactor to form a mixture. The mixture was stirred at 600 revolutions per minute (rpm) and maintained at approximately 40° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate to be 4.0%. The regenerated TS-1 catalyst was recovered by decantation and dried in a vacuum oven at 60° C. for 15 minutes.

Example 46

A fouled TS-1 catalyst (10.0 g, equivalent to 7.8 g fresh TS-1) was added to a 750-mL jacketed glass reactor with a stainless steel cooling coil, thermocouple, mechanical stirrer, addition funnel, N$_2$ purge with gas scrubber, and reflux condenser/cold finger combination. A regeneration solution (350.0 g) having an oxidizing agent concentration of 1.0 wt % hydrogen peroxide, 95.0% methanol and 4.0% de-ionized water was added to the reactor to form a mixture. The mixture was stirred at 600 revolutions per minute (rpm) and maintained at approximately 40° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate to be 0.82%. The regenerated TS-1 catalyst was recovered by decantation and dried in a vacuum oven at 60° C. for 15 minutes.

Comparative Example L

The same fouled catalyst as used in Examples 6-9 was used, but it was not subjected to a regeneration process.
Epoxidation Reaction Using the Regenerated Catalysts from Example 43-46

Allyl chloride (52.0 wt %), methanol (5.2 wt %), 1,2-dichlorobenzene (23.0 wt %), and the regenerated TS-1 catalyst from each of Examples 6-9 (2.00 wt %, equivalent to 1.55 wt % fresh catalyst) were added to a 750-mL jacketed glass reactor with a stainless steel cooling coil, thermocouple, mechanical stirrer, addition funnel, N$_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide, 17.8 wt % total solution, 5.3 wt % H$_2$O$_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a separatory funnel and allowed to separate into a liquid organic phase and a liquid aqueous phase. The liquid organic phase and the liquid aqueous phase were analyzed by GC.

TABLE XVII

| Example | Epi Yield |
| --- | --- |
| 43 | 89.6% |
| 44 | 88.9% |
| 45 | 88.6% |
| 46 | 89.5% |
| Comparative Example L | 86.3% |

What is claimed is:

1. A system, comprising:
a reaction vessel having a multiple liquid phase reaction mixture of an olefin, a peroxide compound, a solvent mixture with an alcohol and a non-reactive co-solvent, a solid phase, and reaction products of the reaction mixture, where the reaction products include an oxirane;

an exchange vessel holding a solid support with active sites to bind iron ions, the exchange vessel having an inlet that carries an organic stream including the olefin and iron ions, where the active sites on the solid support remove iron ions from the organic stream to provide an iron ion concentration of less than one weight percent based on the total weight of the organic stream, and where the exchange vessel has an outlet that connects to the reaction vessel that receives the organic stream having the olefin and the iron ion concentration of less than one weight percent;

a separation vessel having a first outlet, wherein the separation vessel is coupled to the reaction vessel, where an effluent of the multiple liquid phase reaction mixture and reaction products from the reaction vessel separates in the separation vessel into a liquid aqueous phase and a liquid organic phase; and an extraction vessel comprising an extraction solvent capable of extracting oxirane from the liquid aqueous phase, the extraction vessel coupled to the first outlet of the separation vessel, wherein the liquid aqueous phase taken from the outlet of the separation vessel mixes with the extraction solvent to extract oxirane from the liquid aqueous phase.

2. The system of claim 1, where the solid phase has an affinity for the liquid aqueous phase, and where both the liquid aqueous phase and the solid phase form a slurry that is taken from the outlet of the separation vessel and mixes with the extraction solvent to extract at least the oxirane from the liquid aqueous phase.

3. The system of claim 1, wherein the extraction solvent i-sand the non-reactive co-solvent are both 1,2-dichlorobenzene.

4. The system of claim 1, where the solid phase includes a polar group, a charged group or a combination thereof.

5. The system of claim 1, where the active sites of the solid support are represented by the following formula I:

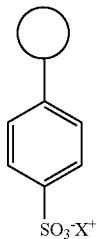

(Formula I)

where $X^+$ is a cation and the circle represents the solid support.

6. The system of claim 1, where the iron ion concentration of the organic stream after removing the iron ions is less than one part per million of the organic stream.

7. The system of claim 1, wherein the solid phase is a titanium silicalite catalyst fouled during a reaction between the olefin and the peroxide compound to produce the oxirane, the system further comprising a regeneration solution in contact with the solid phase, wherein the regeneration solution has an organic compound and an oxidizing agent, the oxidizing agent having a concentration of 0.1 to 50 weight percent based on a total weight of the regeneration solution, exclusive of the solid phase, and wherein the regeneration solution regenerates a first part of the solid phase suspended in the liquid phase with the proviso that the regenerates does not include washing in addition to contact with the regeneration solution to regenerate the solid phase.

8. The system of claim 7, where the oxidizing agent is selected from the group consisting of hydrogen peroxide, ozone, organic peroxide compounds, inorganic peroxide compounds, and combinations thereof.

9. The system of claim 1, where the extraction vessel includes a first outlet through which the extraction solvent with the oxirane and olefin return to the reaction mixture in the reaction vessel.

10. The system of claim 1, further including a distillation unit operation, where the extraction vessel includes a second outlet through which the extraction solvent with the oxirane is transported to the distillation unit operation.

11. The system of claim 1, where the separation vessel includes a second outlet to remove the liquid organic phase from the separation vessel, the second outlet coupled to a distillation unit operation that separates oxirane from a remainder of the liquid organic phase, where the remainder of the liquid organic phase returns to the reaction mixture in the reaction vessel.

12. The system of claim 1, where the oxirane is epichlorohydrin, the olefin is allyl chloride, and the peroxide compound is a hydrogen peroxide solution.

* * * * *

UNITED STATES PATENT AND TRADEMARK OFFICE
CERTIFICATE OF CORRECTION

Page 1 of 1

PATENT NO. : 9,498,762 B2
APPLICATION NO. : 13/983361
DATED : November 22, 2016
INVENTOR(S) : Philip J. Carlberg et al.

It is certified that error appears in the above-identified patent and that said Letters Patent is hereby corrected as shown below:

In the Claims

Column 62, Line 63, delete "i-sand" and replace it with -- and --.

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*